(12) United States Patent
Montano et al.

(10) Patent No.: US 6,753,418 B2
(45) Date of Patent: Jun. 22, 2004

(54) SUPPRESSORS OF HUMAN BREAST CANCER CELL GROWTH

(75) Inventors: Monica Montano, Shaker Heights, OH (US); Bryan Wittmann, Akron, OH (US)

(73) Assignee: Case Western Reserve University, Cleveland, OH (US)

(*) Notice: Subject to any disclaimer, the term of this patent is extended or adjusted under 35 U.S.C. 154(b) by 0 days.

(21) Appl. No.: 09/972,758

(22) Filed: Oct. 5, 2001

(65) Prior Publication Data

US 2002/0160497 A1 Oct. 31, 2002

Related U.S. Application Data

(60) Provisional application No. 60/238,187, filed on Oct. 5, 2000.

(51) Int. Cl.[7] .................. C07H 21/02; C12N 15/00; C12N 1/20; C12P 21/06
(52) U.S. Cl. ............... 536/23.1; 435/69.1; 435/252.3; 435/320.1
(58) Field of Search .................. 536/23.1; 435/69.1, 435/252.3, 320.1

(56) References Cited

U.S. PATENT DOCUMENTS

| 4,683,202 A | * | 7/1987 | Mullis et al. |
| 4,889,806 A | * | 12/1989 | Olson |
| 5,912,143 A | * | 6/1999 | Bandman et al. |
| 2003/0073623 A1 | * | 4/2003 | Drmanac et al. |

FOREIGN PATENT DOCUMENTS

| WO | 9842739 | * | 3/1998 |
| WO | 98/48016 | | 10/1998 |
| WO | 00/11166 | | 3/2000 |

OTHER PUBLICATIONS

Bowie et al (Science, 1990, 247:1306–1310).*
Burgess et al (J. Cell Bio., 1990, 111:2129–2138).*
Lazar et al (Mol. Cell. Biol., 1988, 8:1247–1252).*
Bork (Genome Research, 2000, 10:398–400).*
Harris et al. (J. Am. Soc. Nephrology, 1995, 1125–1133).*
Ahn et al (Nature Genetics 3(4):283–291).*
Cawthorn et al (Genomics, 1991)9(3):446–460).*
Beihringer Mannheim Biochemicals, 1994 Catalog, p. 93).*
Sambrook et al (Molecular Cloning, a Laboratory Manual, 1989, Cold Spring Harbor Press, p. 16.3–4.*

"Cloning of Hexamethylene–bis–acetamide–inducible Transcript, HEXIM1, in Human Vascular Smooth Muscle Cells" by Kusuhara, *Biomedical Research*, 20 (5) 273–279, after Oct. 7, 1999.

GenBank Accession No. NM_00640, Dec. 19, 2001.
GenBank Accession No. AB021179, Dec. 5, 2000.
GenBank Accession No. XM_008348, Dec. 10, 2001.
GenBank Accession No. AK023624, Sep. 29, 2000.
GenBank Accession No. BC006460, Jul. 12, 2001.
GanBank Accession No. XM_038658, Dec. 10, 2001.
GanBank Accession No. BC022111, Jan. 28, 2002.

"Lysophospholipid Growth Factors in the Initiation, Progression, Metastases, and Management of Ovarian Cancer" by Fang, et la., *Annals New York Academy of Sciences*, Apr. 2000, vol. 905, pp. 188–208.

"Optimization of an mCF7–E3 Cell Proliferation Assay and Effects of Environmental Pollutants and Industrial Chemicals" by Desaulniers, et al., *Toxicology in Vitro* 12(1998) 409–422.

"American Ginseng and Breast Cancer Therapeutic Agents Synergistically Inhibit MCF–7 Breast Cancer Cell Growth" by Duda, et al., *Journal of Surgical Oncology*, 1999; 72:230–239.

"An Abundant Transcript Induced in Differentiating Human Endothelial Cells Encodes a Polypeptide with Structural Similarities to G–protein–coupled Receptors" by Hla, et al., *The Journal of Biological Chemistry*, vol. 265, No. 16, Jun. 5, 1990, pp. 9308–9313.

* cited by examiner

*Primary Examiner*—Susan Ungar
(74) *Attorney, Agent, or Firm*—Calfee, Halter & Griswold LLP

(57) ABSTRACT

Molecular tools for differentiating normal breast tissue and cells from cancerous breast tissue and cells are provided. The tools are derived from a novel tumor suppressor gene which encodes a protein referred to hereinafter as the "EDG1" protein. One tool is an isolated polynucleotide which encodes the EDG1 protein. The other tool is an antibody which is immunospecific for the EDG1 protein. Methods of detecting cancerous cells which employ the antibody and polynucleotide are also provided. Methods for decreasing proliferation of breast cancer cells, prostate cancer cells, testicular cancer cells, and ovarian cancer cells are also provided. Such method comprises increasing levels of the EDG1 protein in such cells.

3 Claims, 14 Drawing Sheets

FIG. 1A

SEQUENCE OF EDG1

| atg | gcc | gag | cca | ttc | ttg | tca | gaa | tat | caa | cac | cag | cct | caa | act | agc | |
|-----|-----|-----|-----|-----|-----|-----|-----|-----|-----|-----|-----|-----|-----|-----|-----|---|
| M | A | E | P | F | L | S | E | Y | Q | H | Q | P | Q | T | S | 1 |

| aac | tgt | aca | ggt | gct | gct | gct | gtc | cag | gaa | gag | ctg | aac | cct | gag | cgc | |
|-----|-----|-----|-----|-----|-----|-----|-----|-----|-----|-----|-----|-----|-----|-----|-----|---|
| N | C | T | G | A | A | A | V | Q | E | E | L | N | P | E | R | 32 |

| ccc | cca | ggc | gcg | gag | gag | cgg | gtg | ccc | gag | gag | gac | agt | agg | tgg | caa | |
|-----|-----|-----|-----|-----|-----|-----|-----|-----|-----|-----|-----|-----|-----|-----|-----|---|
| P | P | G | A | E | E | R | V | P | E | E | D | S | R | W | Q | 48 |

| tcg | aga | gcg | ttc | ccc | cag | ttg | ggt | ggc | cgt | ccg | ggg | ccg | gag | ggg | gaa | |
|-----|-----|-----|-----|-----|-----|-----|-----|-----|-----|-----|-----|-----|-----|-----|-----|---|
| S | R | A | F | P | Q | L | G | G | R | P | G | P | E | G | E | 64 |

| ggg | agc | ctg | gaa | tcc | caa | cca | cct | ccc | ttg | cag | acc | cag | gcc | tgt | cca | |
|-----|-----|-----|-----|-----|-----|-----|-----|-----|-----|-----|-----|-----|-----|-----|-----|---|
| G | S | L | E | S | Q | P | P | P | L | Q | T | Q | A | C | P | 80 |

| gaa | tct | agc | tgc | ctg | aga | gag | ggc | gag | aag | ggc | cag | aat | ggg | gac | gac | |
|-----|-----|-----|-----|-----|-----|-----|-----|-----|-----|-----|-----|-----|-----|-----|-----|---|
| E | S | S | C | L | R | E | G | E | K | G | Q | N | G | D | D | 96 |

| tcg | tcc | gct | ggc | ggc | gac | ttc | ccg | ccg | ccg | gca | gaa | gtg | gaa | ccg | acg | |
|-----|-----|-----|-----|-----|-----|-----|-----|-----|-----|-----|-----|-----|-----|-----|-----|---|
| S | S | A | G | G | D | F | P | P | P | A | E | V | E | P | T | 112 |

| ccc | gag | gcc | gag | ctg | ctc | gcc | cag | cct | tgt | cat | gac | tcc | gag | gcc | agt | |
|-----|-----|-----|-----|-----|-----|-----|-----|-----|-----|-----|-----|-----|-----|-----|-----|---|
| P | E | A | E | L | L | A | Q | P | C | H | D | S | E | A | S | 128 |

| aag | ttg | ggg | gct | cct | gcc | gca | ggg | ggc | gaa | gag | gag | tgg | gga | cag | cag | |
|-----|-----|-----|-----|-----|-----|-----|-----|-----|-----|-----|-----|-----|-----|-----|-----|---|
| K | L | G | A | P | A | A | G | G | E | E | E | W | G | Q | Q | 144 |

| cag | aga | cag | ctg | ggg | aag | aaa | aaa | cat | aag | aga | cgc | ccg | tcc | aag | aag | |
|-----|-----|-----|-----|-----|-----|-----|-----|-----|-----|-----|-----|-----|-----|-----|-----|---|
| Q | R | Q | L | G | K | K | K | H | K | R | R | P | S | K | K | 160 |

| aag | cgg | cat | tgg | aaa | ccg | tac | tac | aag | ctg | aac | tgg | gaa | gag | aag | aaa | |
|-----|-----|-----|-----|-----|-----|-----|-----|-----|-----|-----|-----|-----|-----|-----|-----|---|
| K | R | H | W | K | P | Y | Y | K | L | N | W | E | E | K | K | 176 |

| aag | ttc | gac | gag | aaa | cag | agc | ctt | cga | gct | tca | agg | atc | cga | gcc | gag | |
|-----|-----|-----|-----|-----|-----|-----|-----|-----|-----|-----|-----|-----|-----|-----|-----|---|
| K | F | D | E | K | Q | S | L | R | A | S | R | I | R | A | E | 192 |

| atg | ttc | gcc | aag | ggc | cag | ccg | gtc | gcg | ccc | tat | aac | acc | acg | cag | ttc | |
|-----|-----|-----|-----|-----|-----|-----|-----|-----|-----|-----|-----|-----|-----|-----|-----|---|
| M | F | A | K | G | Q | P | V | A | P | Y | N | T | T | Q | F | 208 |

| ctc | atg | gat | gat | cac | gac | cag | gag | gag | ccg | gat | ctc | aaa | acc | ggc | ctg | |
|-----|-----|-----|-----|-----|-----|-----|-----|-----|-----|-----|-----|-----|-----|-----|-----|---|
| L | M | D | D | H | D | Q | E | E | P | D | L | K | T | G | L | 224 |

| tac | tcc | aag | cgg | gcc | gcc | gcc | aaa | tcc | gac | gac | acc | agc | gat | gac | gac | |
|-----|-----|-----|-----|-----|-----|-----|-----|-----|-----|-----|-----|-----|-----|-----|-----|---|
| Y | S | K | R | A | A | A | K | S | D | D | T | S | D | D | D | 240 |

Fig. 1B

```
ttc atg gaa gaa ggg ggt gag gag gat ggg ggc agc gat ggg atg gga
 F   M   E   E   G   G   E   E   D   G   G   S   D   G   M   G   256 ggg gac ggc agc gag ttt ctg cag cgg gac ttc tcg gag acg tac gag
 G   D   G   S   E   F   L   Q   R   D   F   S   E   T   Y   E   272 cgg tac cac acg gag agc ctg cag aac atg agc aag cag gag ctc atc
 R   Y   H   T   E   S   L   Q   N   M   S   K   Q   E   L   I   288 aag gag tac ctg gaa ctg gag aag tgc ctc tcg cgc atg gag gac gag
 K   E   Y   L   E   L   E   K   C   L   S   R   M   E   D   E   304 aac aac cgg ctg cgg ctg gag agc aag cgg ctg ggt ggc gac gac gcg
 N   N   R   L   R   L   E   S   K   R   L   G   G   D   D   A   320 cgt gtg cgg gag ctg gag ctg gag ctg gac cgg ctg cgc gcc gag aac
 R   V   R   E   L   E   L   E   L   D   R   L   R   A   E   N   336 ctc cag ctg ctg acc gag aac gaa ctg cac cgg cag cag gag cga gcg
 L   Q   L   L   T   E   N   E   L   H   R   Q   Q   E   R   A   352 ccg ctt tcc aag ttt gga gac tag
 P   L   S   K   F   G   D   *
                                                                 359
```

Fig. 2A
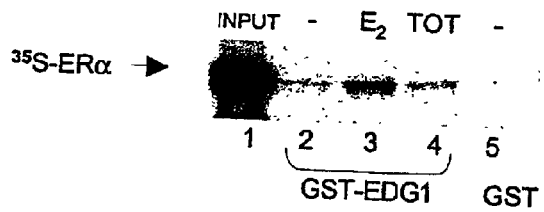
Fig. 2B
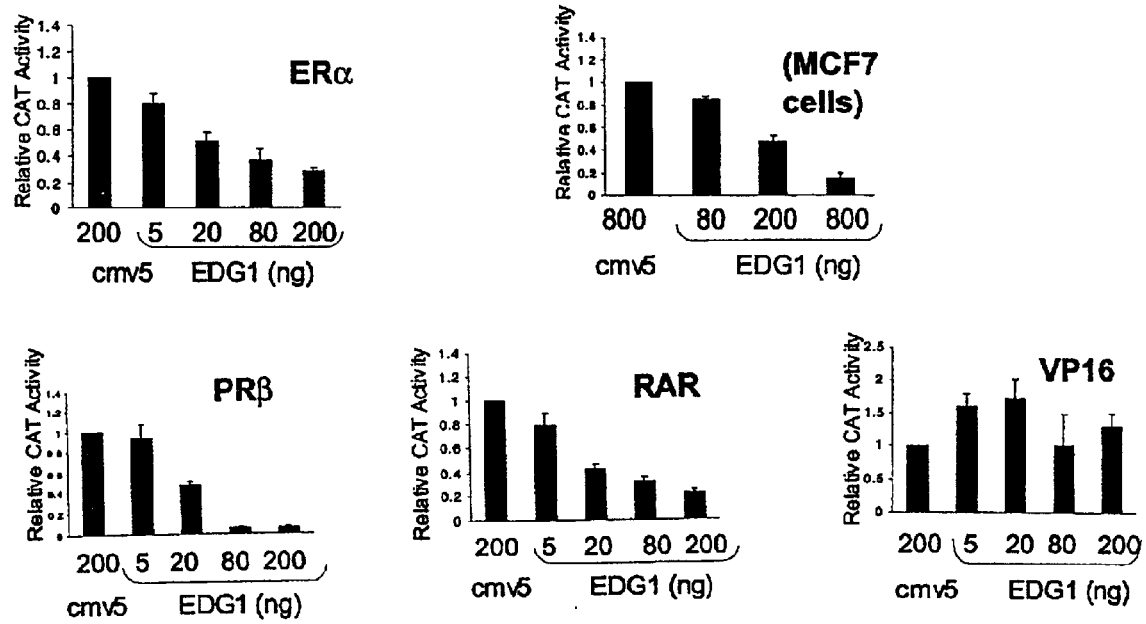
Fig. 2C
 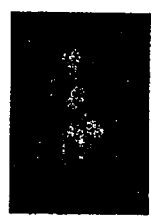  

Fig. 3C
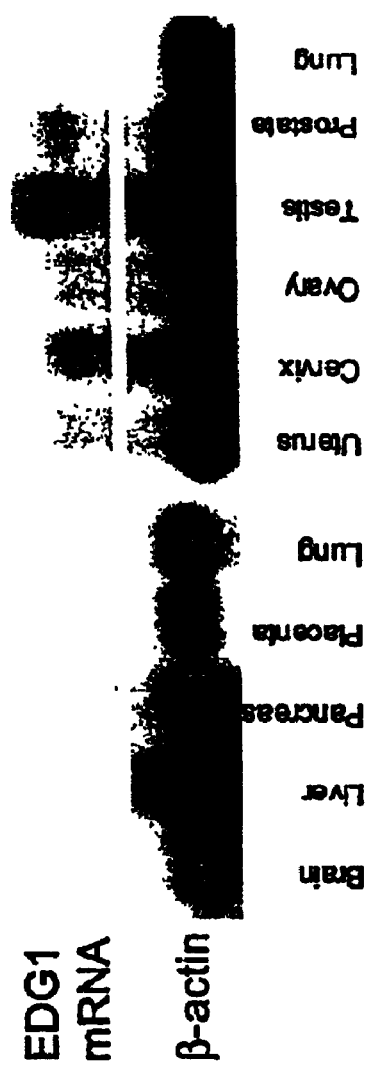

Fig. 4A
MCF10  MCF7 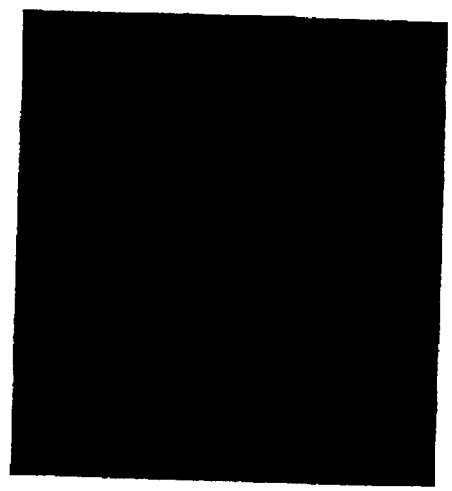

Fig. 4B
MCF7
EGF (16 h)
E₂ (16h)
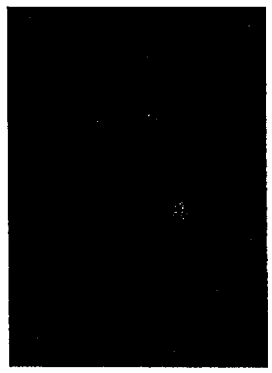
E₂ (12h)
ctrl
E₂ (24h)
E₂ (20h)

SEQUENCE LISTING

<160> NUMBER OF SEQ ID NOS: 7

<210> SEQ ID NO 1
<211> LENGTH: 1080
<212> TYPE: DNA
<213> ORGANISM: Homo sapiens

<400> SEQUENCE: 1

| | |
|---|---|
| atggccgagc cattcttgtc agaatatcaa caccagcctc aaactagcaa ctgtacaggt | 60 |
| gctgctgctg tccaggaaga gctgaaccct gagcgccccc caggcgcgga ggagcgggtg | 120 |
| cccgaggagg acagtaggtg gcaatcgaga gcgttccccc agttgggtgg ccgtccgggg | 180 |
| ccggaggggg aagggagcct ggaatcccaa ccacctccct tgcagaccca ggcctgtcca | 240 |
| gaatctagct gcctgagaga gggcgagaag ggccagaatg gggacgactc gtccgctggc | 300 |
| ggcgacttcc cgccgccggc agaagtggaa ccgacgcccg aggccgagct gctcgcccag | 360 |
| ccttgtcatg actccgaggc cagtaagttg ggggctcctg ccgcagggg cgaagaggag | 420 |
| tggggacagc agcagagaca gctggggaag aaaaaacata agagacgccc gtccaagaag | 480 |
| aagcggcatt ggaaaccgta ctacaagctg aactgggaag agaagaaaaa gttcgacgag | 540 |
| aaacagagcc ttcgagcttc aaggatccga gccgagatgt tcgccaaggg ccagccggtc | 600 |
| gcgccctata acaccacgca gttcctcatg gatgatcacg accaggagga gccggatctc | 660 |
| aaaaccggcc tgtactccaa gcgggccgcc gccaaatccg acgacaccag cgatgacgac | 720 |
| ttcatggaag aaggggggtga ggaggatggg ggcagcgatg ggatgggagg ggacggcagc | 780 |
| gagtttctgc agcgggactt ctcggagacg tacgagcggt accacacgga gagcctgcag | 840 |
| aacatgagca agcaggagct catcaaggag tacctggaac tggagaagtg cctctcgcgc | 900 |
| atggaggacg agaacaaccg gctgcggctg gagagcaagc ggctgggtgg cgacgacgcg | 960 |
| cgtgtgcggg agctggagct ggagctggac cggctgcgcg ccgagaacct ccagctgctg | 1020 |
| accgagaacg aactgcaccg gcagcaggag cgagcgccgc tttccaagtt tggagactag | 1080 |

<210> SEQ ID NO 2
<211> LENGTH: 359
<212> TYPE: PRT
<213> ORGANISM: Homo sapiens

<400> SEQUENCE: 2

Met Ala Glu Pro Phe Leu Ser Glu Tyr Gln His Gln Pro Gln Thr Ser
1               5                   10                  15

Asn Cys Thr Gly Ala Ala Ala Val Gln Glu Glu Leu Asn Pro Glu Arg
            20                  25                  30

Pro Pro Gly Ala Glu Glu Arg Val Pro Glu Glu Asp Ser Arg Trp Gln
        35                  40                  45

```
Ser Arg Ala Phe Pro Gln Leu Gly Gly Arg Pro Gly Pro Glu Gly Glu
 50                  55                  60
Gly Ser Leu Glu Ser Gln Pro Pro Leu Gln Thr Gln Ala Cys Pro
 65                  70                  75                  80
Glu Ser Ser Cys Leu Arg Glu Gly Glu Lys Gly Gln Asn Gly Asp Asp
                 85                  90                  95
Ser Ser Ala Gly Gly Asp Phe Pro Pro Ala Glu Val Glu Pro Thr
            100                 105                 110
Pro Glu Ala Glu Leu Leu Ala Gln Pro Cys His Asp Ser Glu Ala Ser
            115                 120                 125
Lys Leu Gly Ala Pro Ala Ala Gly Gly Glu Glu Trp Gly Gln Gln
130                 135                 140
Gln Arg Gln Leu Gly Lys Lys His Arg Arg Pro Ser Lys Lys
145                 150                 155                 160
Lys Arg His Trp Lys Pro Tyr Tyr Lys Leu Thr Trp Glu Glu Lys Lys
                165                 170                 175
Lys Phe Asp Glu Lys Gln Ser Leu Arg Ala Ser Arg Ile Arg Ala Glu
            180                 185                 190
Met Phe Ala Lys Gly Gln Pro Val Ala Pro Tyr Asn Thr Thr Gln Phe
195                 200                 205
Leu Met Asp Asp His Asp Gln Glu Glu Pro Asp Leu Lys Thr Gly Leu
210                 215                 220
Tyr Ser Lys Arg Ala Ala Ala Lys Ser Asp Asp Thr Ser Asp Asp Asp
225                 230                 235                 240
Phe Met Glu Glu Gly Glu Glu Asp Gly Ser Asp Gly Met Gly
                245                 250                 255
Gly Asp Gly Ser Glu Phe Leu Gln Arg Asp Phe Ser Glu Thr Tyr Glu
            260                 265                 270
Arg Tyr His Thr Glu Ser Leu Gln Asn Met Ser Lys Gln Glu Leu Ile
            275                 280                 285
Lys Glu Tyr Leu Glu Leu Glu Lys Cys Leu Ser Arg Met Glu Asp Glu
            290                 295                 300
Asn Asn Arg Leu Arg Leu Glu Ser Lys Arg Leu Gly Gly Asp Asp Ala
305                 310                 315                 320
Arg Val Arg Glu Leu Glu Leu Glu Leu Asp Arg Leu Arg Ala Glu Asn
                325                 330                 335
Leu Gln Leu Leu Thr Glu Asn Glu Leu His Arg Gln Gln Glu Arg Ala
            340                 345                 350
Pro Leu Ser Lys Phe Gly Asp
            355

<210> SEQ ID NO 3
<211> LENGTH: 19
<212> TYPE: PRT
<213> ORGANISM: Homo sapiens

<400> SEQUENCE: 3

Lys His Arg Arg Pro Ser Lys Lys Arg His Trp Lys Pro Tyr
 1               5                  10                  15

Tyr Lys Leu

<210> SEQ ID NO 4
<211> LENGTH: 18
<212> TYPE: DNA
<213> ORGANISM: Homo sapiens
```

-continued

```
<400> SEQUENCE: 4
cagtgtgatt tctagagc                                                    18

<210> SEQ ID NO 5
<211> LENGTH: 18
<212> TYPE: DNA
<213> ORGANISM: Homo sapiens

<400> SEQUENCE: 5
agagcagaac tactcaag                                                    18

<210> SEQ ID NO 6
<211> LENGTH: 38
<212> TYPE: DNA
<213> ORGANISM: Homo sapiens

<400> SEQUENCE: 6
acacaggatc cgaattcatg tccggagccc ttgatgtc                              38

<210> SEQ ID NO 7
<211> LENGTH: 42
<212> TYPE: DNA
<213> ORGANISM: Homo sapiens

<400> SEQUENCE: 7
acacaggatc cagtcgacta agaccagtca gtggttgctc ct                         42
```

SUPPRESSORS OF HUMAN BREAST CANCER CELL GROWTH

CROSS REFERENCE TO RELATED APPLICATIONS

This invention claims benefit to U.S. Provisional Patent Application Serial No. 60/238,187 filed Oct. 5, 2000, now abandoned.

This invention was made, at least in part, with government support under National Institutes of Health Grant No. CA80959. The U.S. government has certain rights in the invention.

BACKGROUND

Breast cancer is a significant health problem for women in the United States and throughout the world. Despite recent advances in detection and treatment of the disease, breast cancer remains the second leading cause of cancer-related deaths in women. Management of the disease currently relies on a combination of early diagnosis through routine breast screening procedures and aggressive treatment. Such treatment may include surgery, radiotherapy, chemotherapy, hormone therapy or combinations of these therapies.

Ninety-five percent of all breast tumors, at least initially, are dependent on estrogens for growth. Estrogens are steroid hormones that are essential for normal sexual development and functioning of female reproductive organs. Estrogens are also important for growth, differentiation, and functioning of the testis, epididymis and prostate in males. Estrogens also have important non-reproductive effects on bones and the heart. Estrogens comprise a group of natural and synthetic substances. Natural estrogens include estradiol (i.e., 17-β-estradiol or E2), estrone and estriol. Estrogens are sometimes given therapeutically in the form of a conjugate, such as for example, ethinyl estradiol, conjugated estrogens or diethylstilbestrol.

Tissues in the body that are responsive to estrogens are called "estrogen-sensitive" or "estrogen-responsive" tissues and include cells of the urogenital tract, cardiovascular system and skeletal system. The cells that comprise estrogen-sensitive tissues contain estrogen receptors (ER). ER can be of the α type or β type. Estrogens enter cells and bind to ER in the cytoplasm of such cells and an estrogen-ER complex is formed. Herein, a molecule such as estrogen that binds to a receptor is generally called a "ligand." Herein, a receptor such as ER that has formed a complex with a ligand is called a "liganded" receptor.

Once the estrogen ligand binds to ER, the estrogen-ER complex migrates to the nucleus of the cell and binds to specific sequences of DNA within the cellular genome called "estrogen response elements." Such estrogen response elements are located in the promoters of specific genes in the cell nucleus.

Binding of the estrogen-ER complex to estrogen-responsive elements causes activation or suppression of the transcription of the specific genes (Beato, et al., 1995, Cell, 83:851–7.; Katzenellenbogen, et al., 1995, J Steroid Biochem Mol Biol, 53:387–93.; Tsai and O'Malley, 1994, Annu Rev Biochem, 63:451–86.). The activation or suppression of specific gene transcription is one type of molecular and/or cellular response that can result from formation of a ligand-receptor complex. When such a response occurs, the receptor is said to have been "activated."

Estrogen-ER complexes, therefore, act as transcription factors to regulate the expression of these genes. When a ligand binds to a receptor and a molecular and/or cellular response (e.g., transcriptional regulation of genes) occurs, such ligands are referred to as "agonists" and the response produced is called "agonism." Herein, therefore, the term agonist refers to ligands, such as estrogen, that produce the molecular and/or cellular responses.

Estrogens and ER play significant roles in certain human cancers, breast cancer being one specific example. Cells in female breast tissue normally contain ER. Interaction of estrogens with ER in breast cells normally causes the breasts to grow at puberty and again during pregnancy. Since breast cells normally contain ER, it is not surprising that cells comprising tumors of the breast also contain ER. Ninety-five percent of all breast tumors, at least initially, have ER and are dependent on estrogens for growth. In such breast tumor cells, estrogens acting via the ER, dramatically escalate proliferative and metastatic activity (Osborne, et al., 1980, Cancer, 46:2884–8.).

Treatment of such ER-positive breast tumors comprises administration to the individual with the tumor, compounds such as tamoxifen (TOT). TOT can also administered to individuals who may be at high risk for developing breast tumors in the future, for the purpose of prevention of such tumors. Chemically, tamoxifen is one of a number of compounds referred to as triphenyethylene derivatives. Tamoxifen is a mainstay of breast cancer treatment and inhibits the proliferation promoting effect of estrogens (Katzenellenbogen, et al., 1995, J Steroid Biochem Mol Biol, 53:387–93.; Osborne, et al., 1980, Cancer, 46:2884–8.; Jordan and Murphy, 1990, Endocr Rev, 11:578–610.). Like estrogens, TOT binds to ER and, therefore, is also an ER ligand. Unlike estrogen binding to ER, however, TOT binding to ER does not result in production of significant molecular and/or cellular responses. The changes in gene expression resulting from TOT binding to ER are significantly less in magnitude than those resulting from estrogen binding to ER. Such decreased responses are referred to as "partial agonism." Ligands such as TOT, that result in partial agonism, are referred to as "partial agonists."

Of significance is that binding of ER by TOT prevents estrogens from producing their effect on ER (i.e., the partial agonist precludes effects of the agonist). Since estrogens are prevented from producing a molecular and/or cellular response through the ER, the response produced in the presence of both estrogens and TOT will be partial agonism, rather than agonism. Such partial agonism is the basis by which TOT impairs breast tumor growth (i.e., by blocking the agonist effects of estrogens).

With regard to TOT, while it is effective in preventing proliferation of ER-positive breast tumor cells (i.e., cells that contain ER) in the early stages of breast cancer treatment, such ER-positive tumor cells invariably develop resistance to TOT. That is, after a time (e.g., 5 years), TOT is no longer effective in preventing estrogen stimulation of tumor proliferation and, in fact, causes stimulation of proliferation of ER-positive tumor cells.

The high mortality observed in breast cancer patients indicates that additional methods and tools for diagnosing and treating breast cancer are needed. Methods and tools for differentiating between normal breast tissue and cells and cancerous breast tissue and cells are desirable. Additional methods and tools for reducing or inhibiting the growth or proliferation of breast cancer cells are also desirable.

SUMMARY OF THE INVENTION

The present invention provides tools and methods for differentiating normal breast tissue and cells from cancerous breast tissue and cells. The tools are derived from a novel tumor suppressor gene designated as Estrogen Downregulated Gene (EDG1) that is down-regulated by estrogen in mammary epithelial cells. EDG1 encodes a protein referred to hereinafter as the "EDG1" protein (SEQ. ID. NO.2). In one aspect the tool is an isolated polynucleotide which encodes the EDG1 protein. In one embodiment, the isolated polynucleotide comprises the nucleotide sequence of SEQ ID NO.1. The present invention also relates to fragments of the isolated polynucleotide that can be used as probes or primers for identifying cells that are or are not expressing EDG1.

In another aspect, the tool is a monoclonal antibody which is immunospecific for the EDG1 protein. The antibody may further comprise a detectable label, such as a fluorescent label, a chemiluminescent label, a radiolabel or an enzyme. Also encompassed are hybridoma cells and cell lines that produce such antibody. In another aspect, the tool is a polyclonal sera, antibodies of which bind immunologically to the EDG1 protein.

In another aspect, the present invention provides a method of detecting cancerous cells in an hormone responsive tissue test sample. Preferably, the sample is a prostate tissue, ovarian tissue, testes tissue, uterine tissue, cervical tissue or, more preferably a breast tissue sample. In one embodiment, the method comprises contacting the sample or a protein extract therefrom with at least one antibody to the EDG1 protein under conditions wherein antibody binding to the EDG1 protein occurs; and assaying for the presence or absence of a complex between the antibody and a protein in the sample, wherein a decrease in the level of the antigen-antibody complex, as compared to the levels found in a sample of control cells, indicates that the sample comprises cancerous cells. Preferably, the assay is an immunocytochemical assay which permits determination of the intracellular location of the antigen-antibody complexes. In another embodiment, the method comprises assaying for the presence of EDG1 transcript in the sample, wherein a decrease in the level of the EDG1 transcript in the sample, as compared to the level of the EDG1 transcript in a control sample, denotes that the test sample comprises cancerous cells.

The present invention also relates to the protein encoded by EDG1 and biologically active or immunologically reactive fragments thereof. In one embodiment the EDG1 protein has the amino acid sequence of SEQ ID NO.2. In one embodiment the EDG1 protein fragment has the amino acid sequence of SEQ ID NO.3.

The present invention also provides a method for decreasing proliferation of breast cancer cells, prostate cancer cells, testicular cancer cells, and ovarian cancer cells. Such method comprises increasing levels of the EDG1 protein in such cells. In one embodiment, the cells are contacted with the EDG1 protein or a biologically active equivalent or fragment thereof under conditions permitting uptake of the protein or fragment. In another embodiment, the cells are contacted with (i) a nucleic acid encoding the EDG1 protein, and (ii) a promoter active in the cancer cell, wherein the promoter is operably linked to the region encoding the EDG1 protein, under conditions permitting the uptake of the nucleic acid by the cancer cell. The cancer cell may be derived from an endocrine tissue such as breast, ovary, prostate or testes tissue.

The present invention also provides a method for inhibiting the transcriptional activity of estrogen-liganded ERα in cancer cells. Such method comprises increasing the levels of the EDG1 protein in such cells.

BRIEF DESCRIPTION OF THE FIGURES

FIG. 1. shows the nucleotide sequence, SEQ ID NO.1, of a human EDG1 cDNA and the predicted amino acid sequence, SEQ ID NO.2, of the EDG1 protein.

FIG. 2. Functional interaction of EDG1 with ERα. a, in vitro translated and [$^{35}$S]methionine-labeled Estrogen Receptor α (ERα) was incubated with GST alone or GST-EDG1 bound to Sepharose in the presence of vehicle, $10^{-6}$ M Estradiol ($E_2$) or $10^{-6}$ M trans-hydroxytamoxifen (TOT). Bound protein was eluted and analyzed by 12.5% SDS-polyacrylamide gel electrophoresis. "Input" is an input lane and represents in vitro translated product added in the samples. No interaction of in vitro translated products was observed with GST alone. The autoradiograph is representative of 3 separate experiments. b, CHO cells were transfected with expression vectors for activators (5 ng)/reporter constructs (2 μg)—(ERα)/(ERE)$_2$-TATA-CAT or Progesterone Receptor β (PR β)/MMTV-CAT or retinoic acid receptor β (RAR)/DR5-CAT or Gal4-VP16/G5-E1b-CAT. MCF7 cells were transfected with (ERE)$_2$-pS2-CAT. The cells were cotransfected with cmv5 control expression vector or increasing concentration of an expression vector for EDG1 (cmv5-EDG1) as indicated. MCF7 cells, which expresses high endogenous ER, were transfected with (ERE)$_2$-pS2-CAT reporter vector. CHO and MCF7 cells were also transfected with a β-galactosidase internal control reporter to correct for transfection efficiency. Cells were then treated for 24 h with $10^{-8}$ M estradiol ($E_2$), $10^{-8}$ R5020, or $10^{-8}$ all trans retinoic acid. Values are the means±S.E. from three separate experiments. c, CHO cells were transfected with the 100 ng of pEGFP-C3-EDG1 vector or pEGFP-C3-PCMT (PCMT is a known non-nuclear protein). For fluorescence images a fluorescein filter was used. (Original images at 400×total magnification).

Figure 5A:
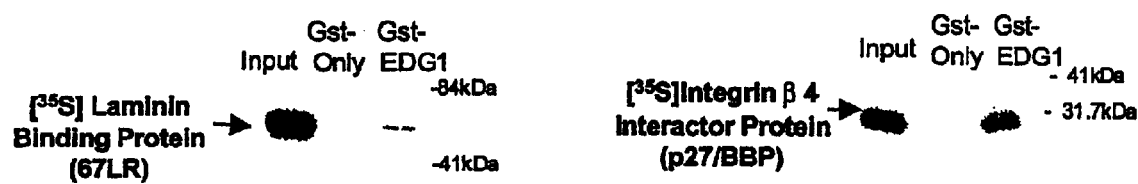
Figure 5B:
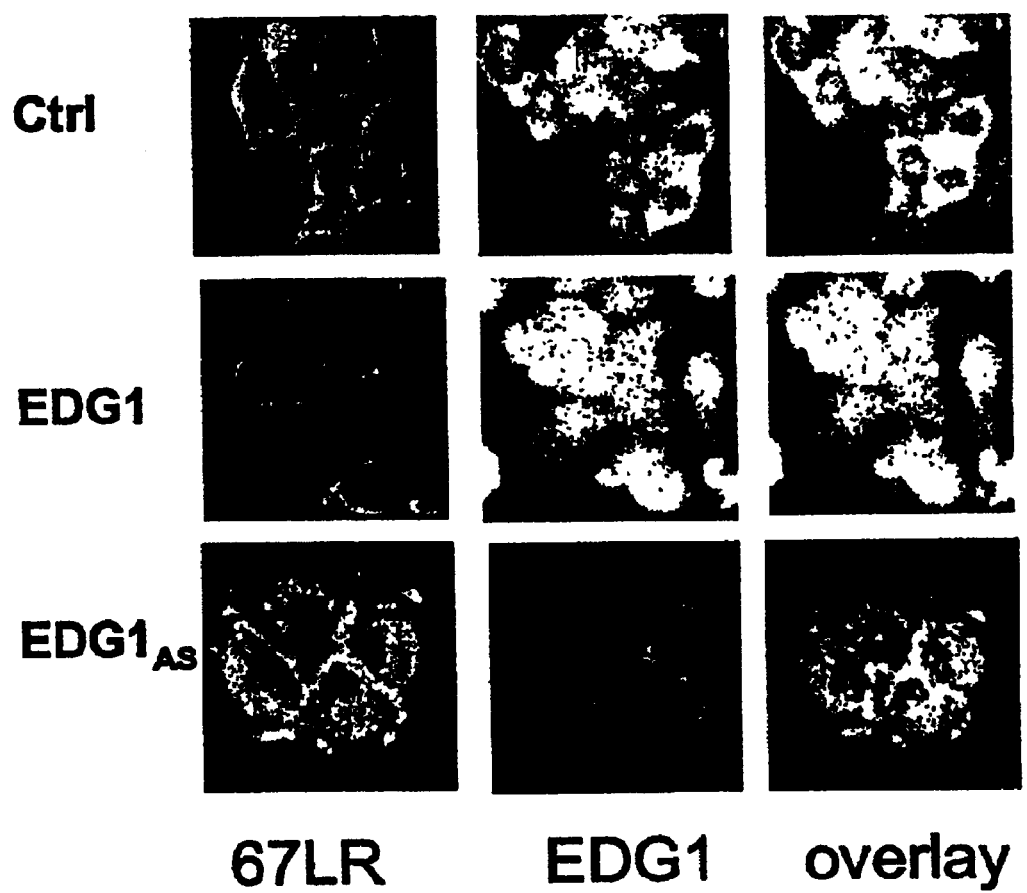
Figure 5C:
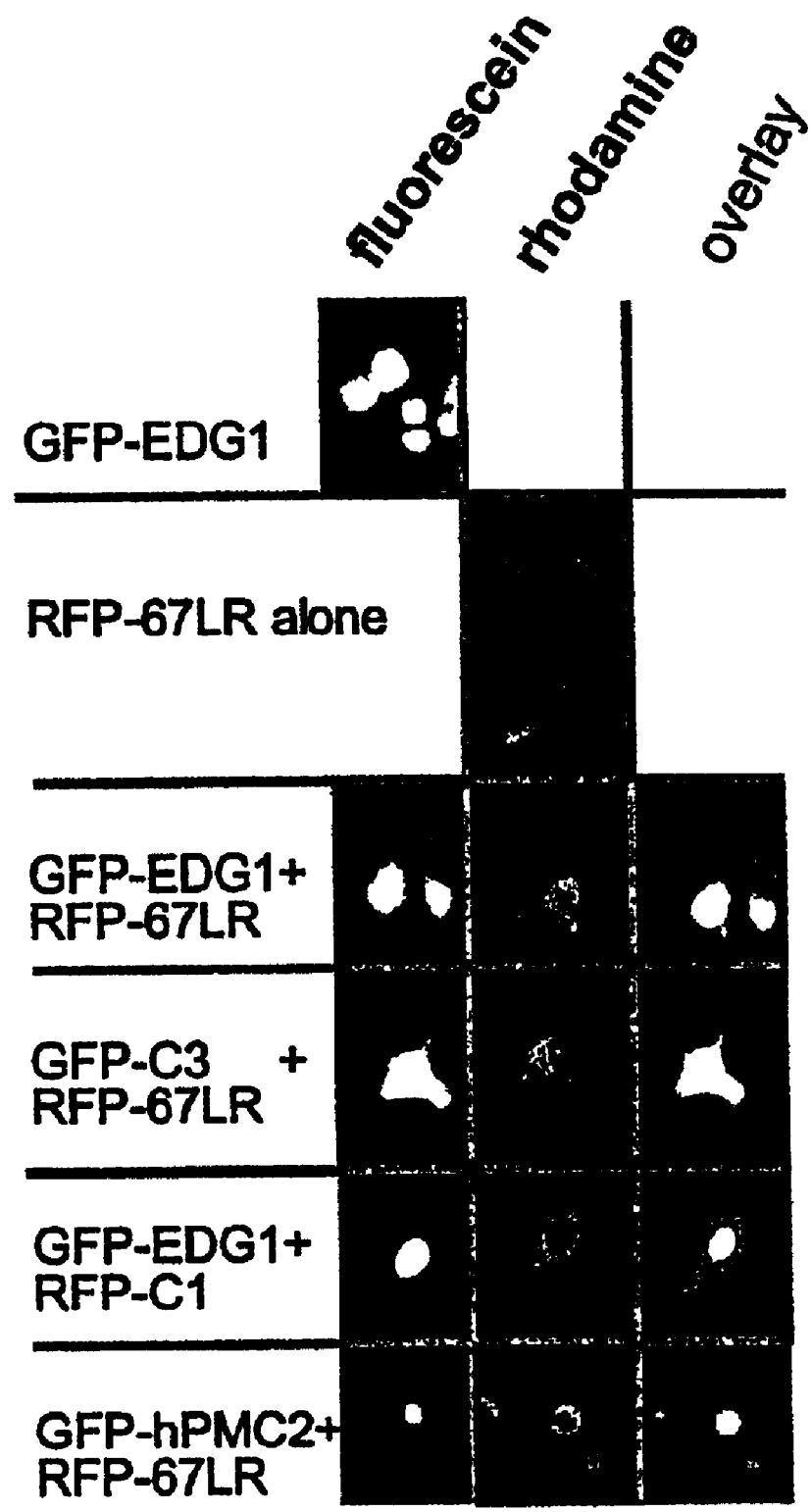

FIG. 5. Functional interaction of EDG1 with binding proteins for components of the extracellular matrix and regulation of anchorage independent growth. a, in vitro translated and [$^{35}$S]methionine-labeled Integrin β4 Receptor or Laminin Binding Protein were incubated with GST alone or GST-EDG1 bound to Sepharose. Bound protein was eluted and analyzed by 12.5% SDS-polyacrylamide gel electrophoresis. The numbers at the right indicate molecular size markers in kilodaltons. "Input" is an input lane and represent 10% of total in vitro translated products added in the samples. The autoradiograph is representative of 3 separate experiments. b, MCF7 infected with control, EDG1 or EDG1$_{As}$ retroviruses were immunostained using 67LR IgG monoclonal mouse antibody and goat, anti-mouse Alexa 594 secondary antibody and EDG1 polyclonal rabbit IgG antibody and goat, anti-rabbit Alexa 488 secondary antibody. c, MCF7 cells were transfected with 100 ng of pEGFP-EDG1, pRFP-67LR, pEGFP-C3, pRFP-C1, or pEGFP-hPMC2 as indicated. pRFP-C1 and pEGFP-C3 are control fluorescent protein vectors without a cDNA insert and pEGFP-hPMC2 is an unrelated nuclear protein. The cells were observed under the microscope 24 h later. For fluorescence images rhodamine or fluorescein filters were used. Original images are at 400× total magnification.

DETAILED DESCRIPTION OF THE INVENTION

Definitions

As used herein the following terms have the following meanings:

"Antibody" means a protein molecule that binds to, cross reacts with, or is immunoreactive with a specific antigen or immunogen. The binding reaction between an antibody and its antigen is specific in that the antibody binds only to an amino acid sequence present within the specific protein (i.e., an epitope). An anti-EDG1 antibody means an antibody molecule that binds to one or more epitopes of the EDG1 protein.

"Biological sample" means a sample of mammalian cells. These cells may be part of a tissue or organ sample obtained, for example, by biopsy, or they may be individual cells, for example, blood cells or cells grown in tissue culture.

"Cancer cell" or "cancerous cell" means a cell in or from a carcinoma.

"Breast cancer" means any of various carcinomas of the breast or mammary tissue.

"cDNA" means a DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein.

"Expression" means the production of a protein or a gene transcript (i.e. mRNA) in a cell.

"Hormone responsive tissue" as used herein refers to tissues that are normally responsive to estrogens or androgens. Hormone responsive tissues include the mammary glands, testes, prostate, uterus and cervix. A tissue which is normally responsive to estrogens or androgens may lose its responsiveness to the hormone. Thus, "hormone responsive tissue" is a broad term as used herein and encompasses both hormone-sensitive and hormone insensitive tissues.

"Estrogen-receptor positive" as used herein refers to a cell that comprises estrogen receptor and is responsive to estrogen and to agents that bind to the estrogen receptor, such as tamoxifen.

"Estrogen-receptor negative" as used herein refers to a cell that is normally responsive to estrogen, such as a mammary epithelial cell, but that contains little to no estrogen receptor. As a result, the estrogen receptor negative cell is estrogen-insensitive and refractory to treatment with tamoxifen.

"Label" means to incorporate into a compound a substance that is readily detected. Such substances include radioactive substances and fluorescent dyes, for example.

"Native" means the nucleic acid of a non-mutated gene or peptide sequence encoded by such a gene as found in a phenotypically normal cell.

"Neoplasia" means the process resulting in the formation and growth of an abnormal tissue that grows by cellular proliferation more rapidly than normal, and continues to grow after the stimuli that initiated the new growth ceases.

"Normal cell" means a non-cancerous cell.

"Proliferation" means growth and reproduction, i.e., division of cells

"Tumor" refers to a spontaneous, new growth of tissue in the body that forms an abnormal mass. Tumors are comprised of cells and such cells are known as tumor cells. Tumors and cells derived from tumors can be either benign or malignant. Cells that are malignant have a variety of properties that benign cells and non-tumor cells do not have. Malignant cells invade, grow and destroy adjacent tissue, metastasize, and usually grow more rapidly than benign tumor cells. "Neoplasm" is essentially synonymous with tumor.

"Tumor suppressor gene" refers to a gene whose expression within a tumor cell suppresses the ability of such cells to grow spontaneously and form an abnormal mass.

All publications and other references mentioned herein are incorporated by reference in their entirety.

EDG1 Protein

The present invention provides a protein referred to hereinafter as EDG1 protein and functional equivalents thereof The EDG1 protein is encoded by the tumor suppressor gene designated Estrogen Downregulated Gene.

Intracellular Localization of EDG1 Protein

EDG1 is localized in different intracellular compartments in normal breast and breast cancer epithelial cells. (See FIG. 4) In normal mammary epithelial cells, represented by the cell line MCF10A, EDG1 is localized primarily in the nucleus. In contrast, lower and more diffuse cytoplasmic staining occurs in MCF7 cells, which are representative of estrogen receptor positive breast cancer epithelial cell (FIG. 4A). Interestingly, EDG1 localized primarily to the nucleus when MCF7 cells were weaned out of their maintenance medium containing phenol red and full serum to phenol red-free media containing charcoal-stripped serum (FIG. 4B). Estradiol, ($E_2$) and epidermal growth factor (EGF) affect the levels and/or intracellular localization of EDG1 protein in breast cancer cells. A slight decrease in EDG1 expression is evident 12 h and 16 h after $E_2$ treatment. (FIG. 4B) After treatment with either Epidermal Growth Factor (EGF) or $E_2$, a decrease in the nuclear localization of EDG1 was evident in MCF7 cells (FIG. 4B). Estrogen- and EGF-induced nuclear export of EDG1 is inhibited by antiestrogen ICI182,780 and Mitogen-Activated Protein Kinase Kinase (MAPKK) inhibitor PD098,059 respectively (data not shown). It was observed that EGF, not $E_2$, induces EDG1 nuclear export in MCF10A cells which expresses very low levels of estrogen receptor (ER) (data not shown).

Interaction of EDG1 Protein with Other Cellular Proteins

EDG1 interacting proteins were identified using the yeast two-hybrid system and the interactions were verified in vitro using GST pull-down assays (FIG. 5A). The strongest interactors from the yeast two hybrid screenings are two proteins involved in cell adhesion—the 67 kD laminin receptor (67LR) and the integrin β4 interactor protein (p27/BBP). Stronger interaction of EDG1 with p27/BBP, when compared to its interaction with 67LR, was observed in GST-pull down assays. Both 67LR and p27/BBP have been proposed to be part of the structural link between extracellular matrix proteins and the cytoskeleton (Biffo S, Sanvito F, Costa S, Preve L, Pignatelli R, Spinardi L, Marchisio PC (1997) Isolation of a novel beta4 integrin-binding protein (p27(BBP)) highly expressed in epithelial cells. *J. Biol. Chem.* 272: 30314–30321; Ardini E, Tagliabue E, Magnifico A, Buto S, Castronovo V, Colnaghi MI, Menard S. (1997) Co-regulation and physical association of the 67-kDa monomeric laminin receptor and the alpha6beta4 integrin. J. Biol. Chem. 272: 2342–2345). The functional relatedness of these two proteins supports the biological relevance of the interaction of EDG1 with these proteins.

Figure 4C:
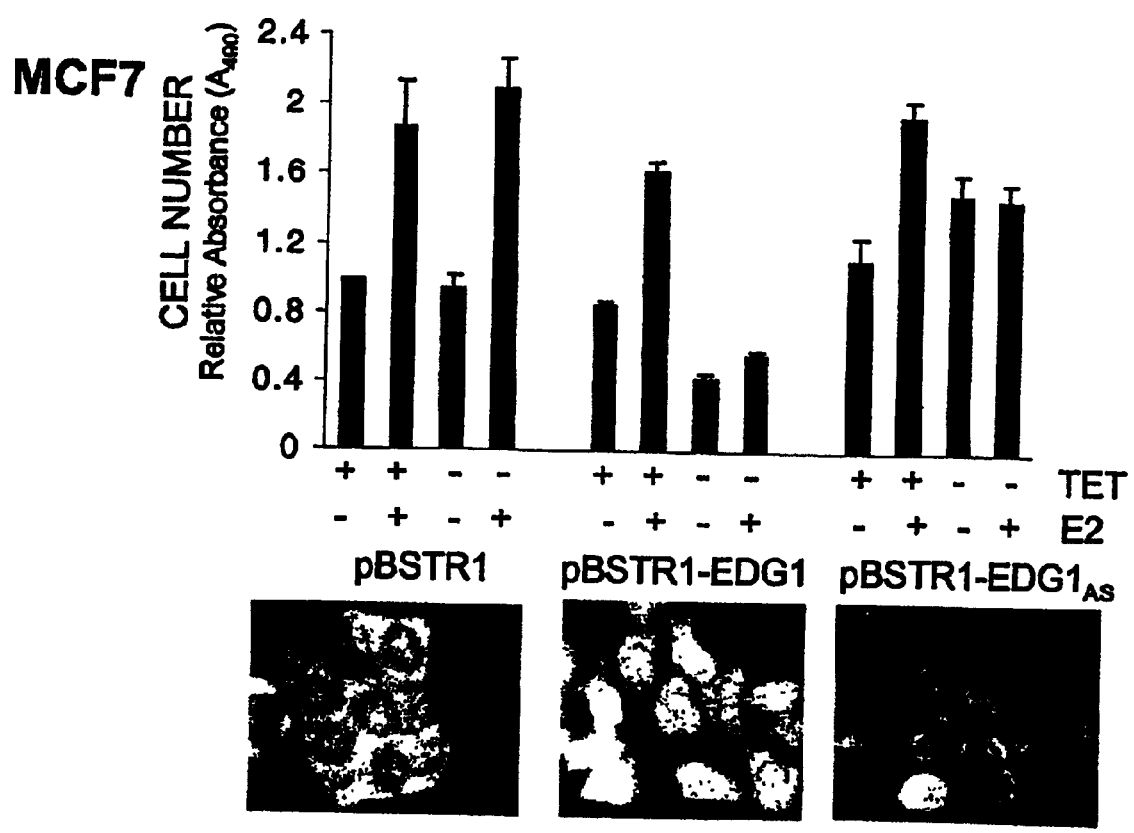
FIG. 4. Regulation of EDG1 intracellular localization and relevance in breast cell growth. a, MCF10A and MCF7 cells were stained for endogenous EDG1 b, MCF7 cells weaned out of phenol-red free- and fall serum-containing medium for 2 weeks and treated with $10^{-9}$ M $E_2$ or 20 ng/ml EGF for the indicated time periods. Cells were then stained for endogenous EDG1. c, MCF7 and MCF10A were infected with control, EDG1, or antisense EDG1 retrovirus in the presence or absence of tetracycline or $10^{-8}$ M Estradiol ($E_2$). Five days after infection, cells were stained for EDG1 expression and cell number was determined using the Cell-Titer 96 Aqueous One Solution Proliferation Assay. Values for cell number are expressed relative to the absorbance in control cells grown in the presence of tetracycline (which is set at 1). Values are the means±S.E. from two separate experiments with triplicate wells for each group. d, MCF7 cells were infected with control, EDG1 or EDG1 $_{AS}$ retrovirus in the presence of 3 µg/ml tetracycline. Twenty-four hours later cells were given fresh media tetracycline. Four days later cells were detached and plated for anchorage independent growth. Values are expressed as the number of colonies formed per number of cells plated×100. Values are expressed relative to the number of colonies/cells plated for cells infected with control retroviruses grown in the presence of tetracycline (which is set at 1). Values are the means±S.E. from two separate experiments with triplicate wells for each group. e, MCF10A and MDA-MD-231 cells were infected with retroviruses and plated for proliferation or immunostaining as described in (d). In a, b, c, and e, cells were stained for endogenous EDG1 using the EDG1 (peptide 152–171) polyclonal rabbit antibody and the goat, anti-rabbit Alexa 488 secondary antibody. Cells were viewed under a fluorescence microscope at 200× magnification. MCF10A cells were also stained with nile red to examine lipid vacoule formation.

To determine the functional consequence of the interaction of EDG1 with 67LR, the expression of 67LR was examined in cells infected with control or EDG1 retroviruses. 67LR is a cell surface-associated protein that interacts specifically and directly with laminin. Increased cell surface expression of 67LR is associated with increased invasiveness and less differentiated phenotypes of several types of human malignancies (Sanvito F, Vivoli F, Gambini S, Santambrogio G, Catena M, Viale E, Veglia F, Donadini A, Biffo S, Marchisio pc. (2000) Expression of a highly conserved protein, p27bbp, during the progression of human colorectal cancer. *Cancer Res.* 60: 510–516; Cress AE, Rabinovitz I, Zhu W, Nagle RB. (1995) The alpha 6 beta 1 and alpha 6 beta 4 integrins in human prostate cancer progression. *Cancer Metastasis Rev.* 14: 219–228.). Increased cell surface expression of 67LR is seen in breast cancer cells treated with estrogen and progesterone (Castronovo V, Taraboletts G, Liotta LA, Sobel M (1989) Modulation of Laminin receptor Expression by Estrogen and Progestins in Human Breast Cancer Cell Lines, *J. Nat. Cancer Instit.* 81: 781–788.). The role of 67LR in breast cancer is not limited to invasion because breast cancer cells undergoing proliferation express increased cell surface 67LR. While 67LR shows primary membrane localization in control cells, cytoplasmic staining was also evident (FIG. 5B). Cells infected with EDG1 retroviruses show an overall decrease in 67LR expression, especially in the membrane. Cells that were treated with estradiol, which induces EDG1 nuclear export, show increased 67LR staining. 67LR has been proposed to originate from a 37 kDa precursor ribosomal protein (37LRP) that can be localized to the nucleus and the cytoplasm (Ardini E, Posole G, Tagliabue E, Magnifico A, Castronovo V, Sobel ME, Colnaghi MI, Menard S. (1998) the 67-kDa laminin receptor originated from a ribosomal protein that acquired a dual function during evloution, *Mol. Biol. Evol.* 15:1017–1025). Acylation of 37LRP leads to the formation of the 67LR dimer and the acquisition of laminin binding capacity. Thus it is possible that EDG1 interferes with 67LR processing. Because the antibody utilized in these experiments does not detect 37LRP, an expression vector wherein 67LR cDNA was cloned in frame with Red Fluorescent Protein (RFP) (pRFP-67LR) was used to explore this possibility. In cells transfected with pRFP-67LR, red fluorescence can be localized throughout the cell (FIG. 4C). Interestingly, when RFP-67LR was coexpressed with green fluorescence protein-tagged EDG1 the localization of red fluorescence was more limited, showing localization primarily in the nucleus. The change in localization was specific to cells expresssing EDG1. No change in red fluorescence localization was evident in cells cotransfected with control GFP expression vector (i.e. no EDG1 cDNA) or with an unrelated protein that we have previously reported to be primarily nuclear (GFP-hPMC2, Montano MM, Wittman, BM, Bianco NR (2000) Identification and Characterization of a Novel Factor that Regulates Quinone Reductase Gene Transcriptional Activity, *J. Biol. Chem.* 275: 34306–34313). The data support an effect of EDG1 on 67LR processing.

Structure of EDG1 Protein

In one embodiment, the EDG1 protein is 359 amino acids in length and comprises the amino acid sequence, SEQ ID NO.2, shown in FIG. 1. The EDG1 protein has a nuclear localization signal spanning residues 150–177. DNAStar analyses predict that the EDG1 protein consists mostly of alpha helices interspersed with turns and coils. EDG1 protein is a highly hydrophilic and highly charged, with a large proportion of the amino acids surface exposed. Many of the alpha helices are amphipathic (i.e. negatively or positively charged). Positive charges come from runs of triple arginine or lysines and negative charges come from triple runs of aspartate or glutamate. These indicate the potential for electrostatic interactions coming about from protein-protein or protein-nucleic acid contacts.

EDG1 Protein Functional Equivalents

The present invention also encompasses functional equivalents of the EDG1 protein that may vary structurally from the EDG1 protein (SEQ. ID. NO.2), but have equivalent function. Such functional equivalents are immunologically cross reactive or biologically active equivalents of the EDG1 protein which comprises SEQ ID NO.2. Such functional equivalents have an altered sequence in which one or more of the amino acids in the corresponding reference sequence is substituted or in which one or more amino acids are deleted from or added to the corresponding reference sequence.

While it is possible to have nonconservative amino acid substitutions, it is preferred that, except for the substitutions that are made to replace cysteine, the substitutions be conservative amino acid substitutions, in which the substituted amino acid has similar structural or chemical properties with the corresponding amino acid in the reference sequence. By way of example, conservative amino acid substitutions involve substitution of one aliphatic or hydrophobic amino acids, e.g., alanine, valine, leucine and isoleucine, with another; substitution of one hydroxyl-containing amino acid, e.g., serine and threonine, with another; substitution of one acidic residue, e.g., glutamic acid or aspartic acid, with another; replacement of one amide-containing residue, e.g., asparagine and glutamine, with another; replacement of one aromatic residue, e.g., phenylalanine and tyrosine, with another; replacement of one basic residue, e.g., lysine, arginine and histidine, with another; and replacement of one small amino acid, e.g., alanine, serine, threonine, methionine, and glycine, with another.

Preferably, the deletions and additions are located at the amino terminus, the carboxy terminus, or both, of SEQ ID NO.2. As a result of the alterations, the EDG1 functional equivalent has an amino acid sequence which is at least 90% identical, preferably at least 95% identical, more preferably at least 97% identical to SEQ ID NO.2 Sequences which are at least 90% identical have no more than 1 alteration, i.e., any combination of deletions, additions or substitutions, per 10 amino acids of the reference sequence. Percent identity is determined by comparing the amino acid sequence of the variant with the reference sequence using MEGALIGN project in the DNA STAR program.

In making such changes, the hydropathic index of amino acids may be considered. The importance of the hydropathic amino acid index in conferring interactive biologic function on a protein is generally understood in the art (Kyte & Doolittle, (1982) A simple method for displaying the hydropathic character of a protein. *J. Mol. Biol.* 157:105–132). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It is known in the art that certain amino acids may be substituted by other amino acids having a similar hydropathic index or score and still result in a protein with similar biological activity, i.e., still obtain a biological functionally equivalent protein. It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

It is understood that an amino acid can be substituted for another having a similar hydrophilicity value and still obtain a biologically active and immunologically cross-reactive protein. As outlined above, amino acid substitutions are generally based on the relative similarity of the amino acid side-chain substituents, for example, their hydrophobicity, hydrophilicity, charge, size, and the like.

The immunologically cross-reactive EDG1 variants immunologically bind to one or more of the antibodies that are raised using the EDG1 protein as an immunogen. The biologically active EDG1 variants inhibit or reduce estrogen-bound estrogen receptor transcriptional activity in MCF7 cells and proliferation of normal mammary epithelial cells or cancerous mammary epithelial cells.

While it is difficult to predict the exact effect of the substitution, deletion or insertion in advance of doing so, for example, when modifying an immune epitope on the EDG1 protein, one skilled in the art will appreciate that the effect will be evaluated by routine screening assays. For example, a change in the immunological character of the EDG1 protein, such as affinity for a given antibody, is measured by a competitive-type immunoassay. Modifications of protein properties such as redox or thermal stability, hydrophobicity, susceptibility to proteolytic degradation, or the tendency to aggregate with carriers or into multimers may be assayed by methods well known to one of skill in the art.

The present invention also encompasses fusion proteins comprising the EDG1 protein or a functional equivalent thereof and a tag, i.e., a second protein or one or more amino acids, preferably from about 2 to 65 amino acids, more preferably from about 34 to about 62 amino acids, which are added to the amino terminus of, the carboxy terminus of, or any point within the amino acid sequence of the EDG1 protein, or a variant of such protein. Typically, such additions are made to stabilize the resulting fusion protein or to simplify purification of an expressed recombinant form of the corresponding EDG1 protein or variant of such protein. Such tags are known in the art. Representative examples of such tags include sequences which encode a series of histidine residues, the epitope tag FLAG, the Herpes simplex glycoprotein D, beta-galactosidase, maltose binding protein, or glutathione S-transferase.

The EDG1 protein and functional equivalents thereof may be produced by conventional peptide synthesizers. The EDG1 proteins and functional equivalents thereof may also be produced using cell-free translation systems and RNA molecules derived from DNA constructs that encode the EDG1 proteins. Alternatively, EDG1 proteins and functional equivalents thereof are made by transfecting host cells with expression vectors that comprise a DNA sequence that encodes the respective EDG1 protein or functional equivalents and then inducing expression of the protein in the host cells. For recombinant production, recombinant constructs comprising a sequence which encodes the EDG1 protein or functional equivalents thereof are introduced into host cells by conventional methods such as calcium phosphate transfection, DEAE-dextran mediated transfection, transvection, microinjection, cationic lipid-mediated transfection, electroporation, transduction, scrape loading, ballistic introduction or infection.

The EDG1 protein and functional equivalents thereof may be expressed in suitable host cells, such as for example, mammalian cells, yeast, bacteria, or other cells under the control of appropriate promoters using conventional techniques. Following transformation of the suitable host strain and growth of the host strain to an appropriate cell density, the cells are harvested by centrifugation, disrupted by physical or chemical means, and the resulting crude extract retained for further purification of the EDG1 protein.

Conventional procedures for isolating recombinant proteins from transformed host cells, such as isolation by initial extraction from cell pellets or from cell culture medium, followed by salting-out, and one or more chromatography steps, including aqueous ion exchange chromatography, size exclusion chromatography steps, and high performance liquid chromatography (HPLC), and affinity chromatography may be used to isolate recombinant EDG1 protein.

EDG1 Polypeptides and Oligopeptides

The present invention also encompasses oligopeptides or polypeptides, referred to hereinafter collectively as "EDG1 polypeptides," that are less than 359 amino acids in length and comprise a consecutive sequence in SEQ ID NO.2. In one aspect, the EDG1 polypeptides are immunologically cross-reactive with the EDG1 protein. Such polypeptides can be used to prepare antibodies that form antigen-antibody complexes with the EDG1 protein. In one embodiment, the EDG1 polypeptide comprises amino acids 152–171 of SEQ ID NO.2. In other words, the EDG1 polypeptide comprises the hydrophilic region, KHRRRPSKKKRHWKPYYKL SEQ ID NO.3.

In another aspect, the EDG1 polypeptide has the biological activity of the native EDG1 protein, i.e., the EDG1 polypeptide has the ability to reduce or inhibit proliferation of a non-cancerous or cancerous mammary epithelial cell.

Polynucleotides

The present invention provides isolated polynucleotides which encode the EDG1 protein or a functional equivalent thereof. The EDG1 polynucleotides may be single-stranded or double stranded. Such polynucleotides may be DNA or RNA molecules In one embodiment the isolated polynucleotide comprises the EDG1 cDNA sequence, SEQ ID NO.1, shown in FIG. 1. Sequence analysis of the EDG1 cDNA clone indicates an open reading frame of 1077 bp (359 amino acids) encoding a 40 kDa protein. The EDG1 polynucleotides are useful for preparing EDG1 proteins.

Figure 3A:
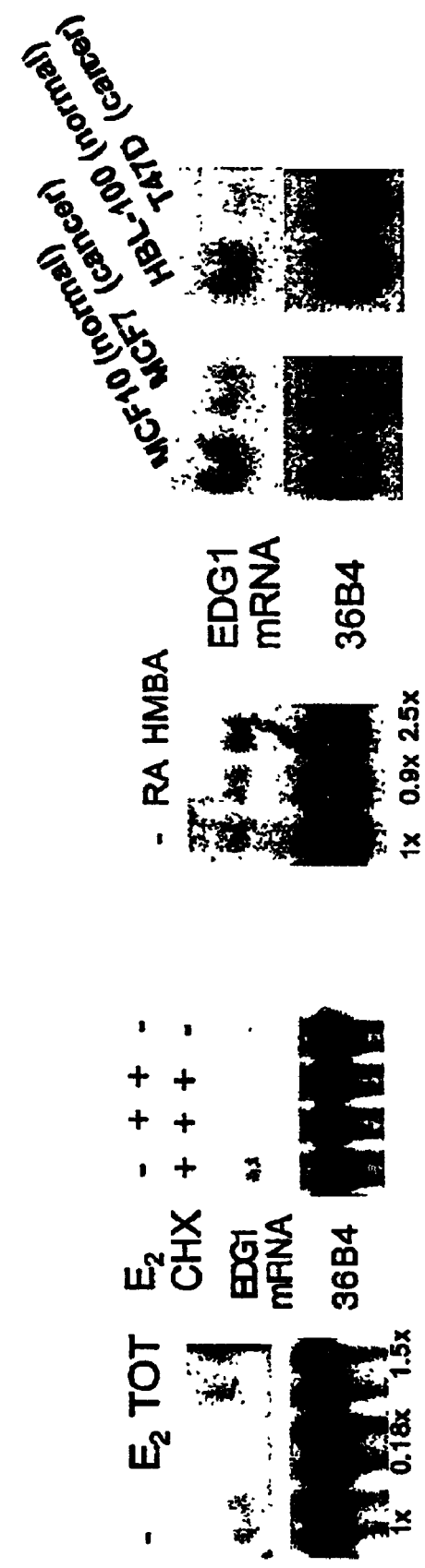
FIG. 3. EDG1 expression and intracellular localization in normal breast and breast cancer tissue and epithelial cells. a, Total RNA was collected from untreated MCF7 cells (−), and cells treated for 24 h with $10^{-9}$ M 17β-Estradiol ($E_2$), $10^{-6}$ M all trans retinoic acid (RA), or 5 mM hexamethylene bisacetanide (HMBA). Total RNA was also collected from different breast epithelial cell lines. The blot was probed with random primer-labeled EDG1 cDNA. To control for RNA loading the same blot was reprobed with 36B4. The autoradiographs are representative of three separate experiments. b, Sections obtained from breast tumor and adjacent normal breast tissue of 3 patients were stained for endogenous EDG1 using the EDG1 (peptide 152–171) polyclonal rabbit antibody and the goat, anti-rabbit Alexa 488 secondary antibody. c, EDG1 expression in human tissues. Master human normal blots (Invitrogen) containing mRNA from different tissues was probed with random primer-labeled EDG1 cDNA. To control for RNA loading the same blot was reprobed with actin. EDG1 and β-actin mRNA levels were quantified using densitometry. EDG1 mRNA levels were normalized to β-actin levels and expressed relative to EDG1 expression in the lung.
Figure 3B:
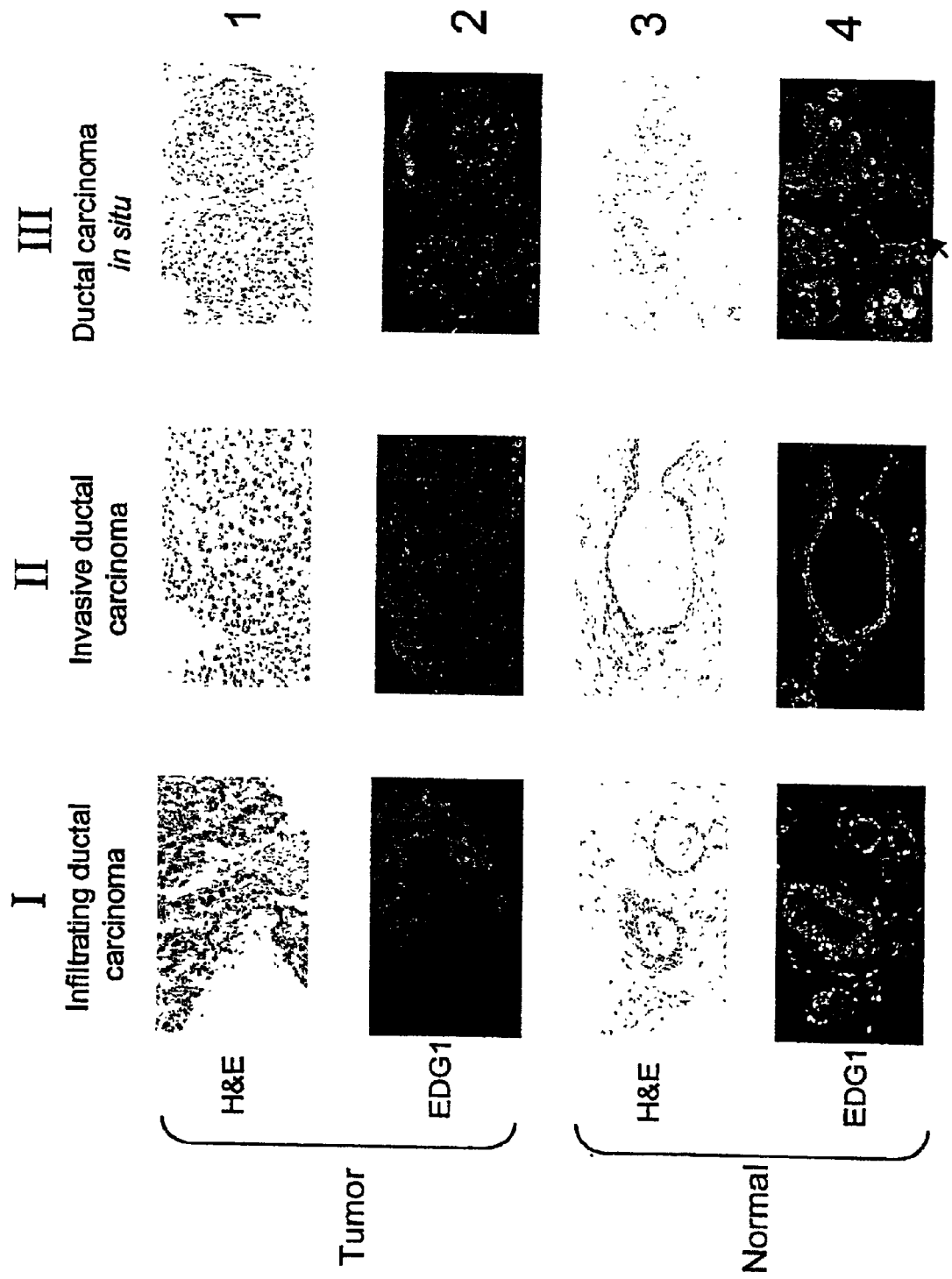

In vivo, EDG1 acts as a tumor suppressor gene. Database searches indicate that EDG1 can be localized to chromosome arm 17q. EDG1 mRNA expression is prevalent in normal mammary epithelial cells and in other human hormone responsive tissues such as the ovary and prostate, and testes (FIG. 2C). Expression of EDG1 mRNA is low in breast cancer epithelial cells. Estradiol or $E_2$ which induces breast cancer cell growth, has an inhibitory effect on EDG1 mRNA expression in breast cancer cells. Conversely, hexamethylene-bis-acetamide (HMBA), which is known to be an inducer of differentiation and apoptosis, upregulates EDG1 mRNA expression in breast cancer cells (FIG. 3A).

The present invention also encompasses isolated polynucleotides whose sequence is the complement of the EDG1 cDNA sequence, SEQ ID NO.1, and polynucleotides that hybridize under stringent conditions, preferably under highly stringent conditions, to the open reading frame sequence of the EDG1 cDNA sequence, SEQ ID NO.1, or the complement thereof. Such hybridization conditions are based on the melting temperature, Tm, of the nucleic acid binding complex or probe, as described in Berger and Kimmel (1987) Guide to Molecular Cloning Techniques, Methods in Enzymology, vol 152, Academic Press. The term "stringent conditions," as used herein, is the "stringency" which occurs within a range from about Tm-5 (5° below the melting temperature of the probe) to about 20° C. below Tm. As used herein, "highly stringent" conditions employ at least 0.2×SSC buffer and at least 65° C. As recognized in the art, stringency conditions can be attained by varying a number of factors such as the length and nature, i.e., DNA or RNA, of the probe; the length and nature of the target sequence, the concentration of the salts and other components, such as formamide, dextran sulfate, and polyethylene glycol, of the hybridization solution. All of these factors may be varied to generate conditions of stringency which are equivalent to the conditions listed above.

Variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

The present invention also relates to polynucleotide encoding a protein having a sequence that is at least 85%, preferably at least 90%, more preferably at least 95%, most preferably at least 97% identical to the amino acid sequences depicted in FIG. 1 and set forth in SEQ ID NO. 2, provided that such protein is an immunologically cross-reactive or biologically reactive equivalent of the EDG1 protein. Such sequences include allelic variants, species variants and other amino acid sequence variants (e.g., including "muteins" or "mutant proteins"), whether naturally-occurring or biosynthetically produced.

Polynucleotides that encode the EDG1 protein and sequences which are the complements thereof are useful tools for designing hybridization probes for screening tissue samples, particularly tissues from patients known to have or suspected of having breast cancer, and for isolating and identifying cDNA clones and genomic clones encoding the EDG1 genes or allelic forms thereof. Such hybridization techniques are known to those of skill in the art. SEQ ID NO. 1, and sequences which are the complement thereof are also useful for designing primers for polymerase chain reaction (PCR), a technique useful for obtaining large quantities of cDNA molecules that encode the EDG1 proteins.

Also encompassed by the present invention, are single stranded polynucleotides, hereinafter referred to as antisense polynucleotides, having sequences which are complementary to the DNA and RNA sequences which encode the EDG1 protein. The term complementary as used herein refers to the natural binding of the polynucleotides, through hydrogen bond formation between complementary nucleotide bases, under permissive salt and temperature conditions by base pairing.

The present invention also provides primers which can be used in PCR to obtain the EDG1 poylnucleotides from cDNA libraries, for screening tissue samples, or for diagnostic purposes. The present invention also encompasses oligonucleotides that are used as primers in polymerase chain reaction (PCR) technologies, reverse transcriptase-PCR (RT-PCR) for example, to amplify transcripts of the genes which encode the EDG1 proteins or portions of such transcripts. Preferably, the primers comprise 12–50 nucleotides, more preferably 15–30 nucleotides. Preferably, the primers have a G+C content of 40% or greater. Such oligonucleotides are at least 98% complementary with a portion of the DNA strand, i.e., the sense strand, which encodes the respective EDG1 or a portion of its corresponding antisense strand. Preferably, the primer has at least 99% complementarity, more preferably 100% complementarity, with such sense strand or its corresponding antisense strand. Primers which have 100% complementarity with the antisense strand of a double-stranded DNA molecule which encodes a EDG1 protein have a sequence which is identical to a sequence contained within the sense strand. The identity of primers which are 15 nucleotides in length and have full complementarity with a portion of the antisense strand of a double-stranded DNA molecule which encodes the EDG1 protein and is determined using the nucleotide sequence, SEQ ID NO:1, shown in FIG. 1.

Such primers for PCR comprise a pair of set of primers. One primer of the pair is called the "forward primer" and is located at the left end of the sequence to be amplified. The second primer of is called the "reverse primer" and is located at the right end of the sequence to be amplified. The forward primer hybridizes to the opposite strand of the template (the DNA to be amplified) than does the reverse primers. Selection of forward and reverse primers, for the purpose of amplifying a sequence of DNA by PCR, is well known to one skilled in the art.

The present invention also encompasses oligonucleotides that are useful as hybridization probes for detecting transcripts of the genes which encode the EDG1 protein Preferably, such oligonucleotides comprise at least 200 nucleotides. Such hybridization probes have a sequence which is at least 90% complementary with a contiguous sequence contained within the sense strand or antisense strand of a double stranded DNA molecule which encodes the EDG1 protein. Such hybridization probes bind to the sense strand or antisense under stringent conditions, preferably under highly stringent conditions. The probes are used in Northern assays to detect transcripts of EDG1 homologous genes and in Southern assays to detect EDG1 homologous genes. The identity of probes which are 200 nucleotides in length and have full complementarity with a portion of the sense or antisense strand of a double-stranded DNA molecule which encodes the EDG1 protein is determined using the nucleotide sequence, SEQ ID NO:1, shown in FIG. 1.

The present invention also encompasses isolated polynucleotides which are alleles of the genes which encode the EDG1 proteins. As used herein, an allele or allelic sequence is an alternative form of the gene which may result from one or more mutations in the sequences which encode the EDG1 proteins. Such mutations typically arise from natural addition, deletion of substitution of nucleotides in the open reading frame sequences Any gene may have none, one, or several allelic forms. Such alleles are identified using conventional techniques, such as for example screening libraries with probes having sequences identical to or complementary with one or more EDG1 polynucleotides.

The present invention also encompasses altered polynucleotides which encode the EDG1 protein or a functional equivalent of the EDG1 protein. Such alterations include deletions, additions, or substitutions. Such alterations may produce silent changes and result in an EDG1 protein having the same amino acid sequence as the EDG1 protein encoded by the unaltered polynucleotide. Such alterations may produce a nucleotide sequence possessing non-naturally occurring codons. For example, codons preferred by a particular prokaryotic or eucaryotic host may be incorporated into the nucleotide sequences shown in FIG. 1 to increase the rate of expression of the proteins encoded by such sequences. Such alterations may also introduce new restriction sites into the sequence or result in the production of a EDG1 protein variant. Typically, such alterations are accomplished using site-directed mutagenesis.

Synthesis of Polynucleotides Encoding EDG1 Proteins or Variants Thereof

Polynucleotides comprising sequences encoding a EDG1 protein or a functional equivalent thereof may be synthesized in whole or in part using chemical methods. Polynucleotides which encode an EDG1 protein, particularly alleles of the genes which encode an EDG1 protein, may be obtained by screening a genomic library or cDNA library with a probe comprising sequences identical or complementary to the sequences shown in FIG. 1 or with antibodies immunospecific for an EDG1 protein to identify clones containing such polynucleotide.

The probes are used in Northern blot or colony hybridization assays under high stringency conditions. Alternatively, polynucleotides encoding EDG1 proteins may be made using polymerase chain reaction (PCR) technology and primers which bind specifically to sequences which are known to encode a EDG1 protein.

Antibodies

The present invention also provides antibodies that are immunospecific for the EDG1 protein. As used herein the term immunospecific means the antibody binds with greater affinity to an EDG1 protein than other proteins that are found in normal breast cells.

The term "antibody" encompasses monoclonal antibodies, polyclonal antibodies, multispecific antibodies (e.g., bispecific antibodies), and antibody fragments, so long as they exhibit the desired biological activity. "Antibody fragments" comprise a portion of a full length antibody, generally the antigen binding or variable region thereof. Examples of antibody fragments include Fab, Fab', F(ab')$_2$, and Fv fragments.

Antibodies raised against EDG1 are produced by immunizing a host animal with an EDG1 protein or an antigenic fragment thereof. Suitable host animals for injection of the protein immunogen include, but are not limited to, rabbits, mice, rats, goats, and guinea pigs. Various adjuvants may be used to increase the immunological response in the host animal. The adjuvant used depends, at least in part, on the host species. For example, guinea pig albumin is commonly used as a carrier for immunizations in guinea pigs. Such animals produce heterogenous populations of antibody molecules, which are referred to as polyclonal antibodies and which may be derived from the sera of the immunized animals.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations, which typically include different antibodies directed against different determinants (epitopes), each monoclonal antibody is directed against a single determinant on the antigen.

The monoclonal antibodies to be used in accordance with the present invention may be made by the hybridoma method, first described by Kohler et al., Nature 256: 495 (1975), in which case the hybridoma cell lines that are obtained secrete the monoclonal antibodies during growth. In order to grow the hybridoma cell lines and obtain the secreted antibodies, the hybridoma cell lines may be grown in cell culture and culture medium containing the monoclonal antibodies collected. Alternatively, the hybridoma cell lines may be injected into, and grown within, the peritoneal cavity of live animals, preferably mice. As the hybridoma cell lines grow within the peritoneal cavity of the animal, the monoclonal antibodies are secreted. This peritoneal fluid, called "ascites," is collected using a syringe to obtain the monoclonal antibodies. Such antibodies may be of any immunoglobulin class including IgG, IgM, IgE, Iga, IgD and any class thereof.

Antibody preparations may be isolated or purified. An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody may be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

Antibodies immunospecific for EDG1 are useful diagnostic markers detecting cancerous epithelial cells in a tissue selected from breast tissue, ovarian tissue, testicular tissue, prostate tissue, uterine tissue and cervical tissue. In accordance with the present invention, it has been shown that cancerous mammary epithelial cells have lower levels of EDG1 protein than non-cancerous mammary epithelial cells. The diagnostic method comprises the steps of contacting a sample of test cells or a protein extract thereof with immunospecific anti-EDG1 antibodies and assaying for the formation of a complex between the antibodies and a protein in the sample. Because EDG1 protein localizes to the nucleus in non-cancerous mammary epithelial cells and, if present, to the cytoplasm of cancerous mammary epithelial cells, it is preferred that the assay be an immunocytochemical assay. The cells may be fixed or premeablized to permit interaction between the antibody and intracellular proteins. Interactions between antibodies and a protein or peptide in the sample are detected by radiometric, colorimetric, or fluorometric means. Detection of the antigen-antibody complex may be accomplished by addition of a secondary antibody that is coupled to a detectable tag, such as for example, an enzyme, fluorophore, or chromophore. Formation of low levels of complex in the test cell as compared to the normal cells indicates that the test cell is cancerous.

Cancer Detection Methods Employing EDG1 Polynucleotides

The EDG1 polynucleotides or fragments are also useful for detecting, defining the borders of, or grading mammary epithelial cell carcinomas in patients known to have or suspected of having a mammary epithelial cell carcinoma. The EDG1 polynucleotides or fragments may also be used to detect cancerous cells in prostate, testicular, and ovarian tissue. In accordance with the present invention, it has been determined that mammary epithelial cell lines derived from mammalian tissues obtained from individuals with breast cancer have lower levels of EDG1 mRNA than mammary epithelial cells derived from normal mammary tissues. In accordance with the present invention, it has also been determined that cells derived from prostate tissue, testicular tissue, and ovarian tissue contain relatively high levels of EDG1 transcript.

Thus, the polynucleotides of the present invention may be used as probes in Northern analysis to identify tissues which have comparatively lower and higher levels of EDG1 mRNA. In such procedures total RNA or mRNA is obtained from the cells that are know to be or suspected of being cancerous and from non-cancerous cells, i.e. breast epithelial cells, testicular epithelial cells, prostate cells, or ovarian cells, preferably from the same patient, and then assayed using the EDG1-designed probe. In general, the non-cancerous cells will be obtained from tissues near but outside the border of the expected carcinoma.

In one example, the coding sequence is radioactively labeled with $^{32}P$ or digoxigenin, and then hybridized in solution to RNA that is isolated from test cells, e.g., mammary epithelial cells suspected of being cancerous, and separated by size using gel electrophoresis and blotted to nitrocellulose paper. After hybridization and washing of the nitrocellulose paper, hybridization of the EDG1 probe to RNA on the nitrocellulose, as revealed by autoradiography, indicates expression of the EDG1 mRNA. Decreased levels of EDG1 mRNA expression in the test cells as compared to levels of EDG1 mRNA present in normal epithelial cells derived from the same type of tissue indicates that the test cells are cancerous.

In another embodiment of the present invention, EDG1 probes, labeled as described above, are used to hybridize directly to test cells, e.g. mammary epithelial cells or tissues suspected of being cancerous, and to normal cells derived from the same type of tissue, i.e. control cells. The cells or tissues are fixed before hybridization, using procedures well known to those skilled in the art. Hybridization is performed under conditions similar to those described above. Detection of hybridization, by autoradiography for example, indicates the presence of EDG1 transcripts within the cells or tissues. A reduced level of EDG1 transcripts in the test tissues or cells as compared to control cells indicates that the test cells are cancerous.

Similarly, EDG1-designed primers may be used in RT-PCR to quantify the amount of EDG1 mRNA in the test tissues and cells. Examples of such primers include, but are not limited to (for EDG1)

```
rt1: cagtgtgatttctagagc, SEQ ID NO. 4, and
rt2: agagcagaactactcaag, SEQ ID NO. 5.
```

Alternatively, EDG1-designed primers may be used to analyze tissue sections from human patients by an RT in situ-PCR hybridization protocol as described Nuovo et al (1994) in Am J. Pathol., 144, 659–666, which is specifically incorporated herein by reference.

Cancer Detection Methods Employing Anti-EDG1 Antibodies

Anti-EDG1 antibodies have a diagnostic use, since simple immunochemical staining of tissue sections, cells, and protein extracts derived from mammary, prostate, testicular, and ovarian tissues can be used to estimate the portion of cells expressing the EDG1 protein. Such a test based on the use of anti-EDG1 antibodies and other standard secondary techniques of visualization will be useful in cancer diagnosis, particularly cancer diagnosis of breast tissue. Such a test of tumor suppressor gene expression might also be useful to the scientific research community.

In a diagnostic method of the present invention, the anti-EDG1 antibodies are used to determine the extent to which EDG1 protein is present in a tissue sample obtained from an individual known to have or suspected of having carcinoma, particularly breast carcinoma. This can be determined using known techniques. Comparison of results obtained from the tissue sample with results obtained from an appropriate control (e.g., cells or tissue of the same type known to have normal EDG1 levels) is carried out. Decreased EDG1 levels are indicative of an increased probability of abnormal cell proliferation or oncogenesis or of the actual occurrence of abnormal proliferation or oncogenesis. It is contemplated that the levels of EDG1 in cancerous cells will be at least 50% less than the level of EDG1 protein in non-cancerous cells, more preferably the levels will be less than 30% of normal levels, most preferably EDG1 will not be expressed. In accordance with the present invention, it has been shown that cells derived from more advanced carcinomas will have lower levels of EDG1 than cells derived from less advanced carcinomas. Thus, the levels of EDG1 in the test cells can be used as a prognostic marker of the carcinoma.

The sample may be untreated, or subjected to precipitation; fractionation, separation, or purification before combining with the anti-EDG1 protein antibody. In those cases where proteins are extracted from the sample, it is preferred that isolated proteins from the sample be attached to a substrate such as a column, plastic dish, matrix, or membrane, preferably nitrocellulose. For isolated protein, the preferred detection method employs an enzyme-linked immunosorbent assay (ELISA) or a Western immunoblot procedure.

Formation of the complex is indicative of the presence of the EDG1 protein in the test sample. Thus, the method is used to determine whether there is a decrease or increase in the levels of the EDG1 protein in a test sample as compared to levels of the EDG1 protein in a control sample and to quantify the amount of the EDG1 protein in the test sample. Deviation between control and test values establishes the parameters for diagnosing the disease.

In accordance with the present invention, it has been determined that EDG1 protein is primarily localized in the nucleus of normal mammary epithelial cells. It has also been determined that EDG1 protein, if present, localizes predominantly in the cytoplasm in cancerous mammary epithelial cells and that the extent of cytoplasmic localization correlates with the stage of the cancer, i.e., more EDG1 protein localizes in cytoplasm of cells derived from advanced carcinomas. Thus, it is preferred that the antibody-based detection methods employ cell tissue sections, since the information obtained from such samples permit not only detection of cancerous cells, but also an assessment of the grade of the tumor that is detected.

Methods of Inhibiting Proliferation of Cancer Cells

The EDG1 polynucleotides and proteins may also be used to block the growth or decrease the proliferation of hormone responsive cancer cells derived from breast tissue, prostate tissue, ovarian tissue, uterine tissue and testicular tissue. The polypeptides may be used to decrease proliferation of both hormone sensitive and hormone insensitive cancer cells that are derived from these tissues, including estrogen receptor positive and estrogen receptor negative breast cancer cells. The EDG1 polynucleotides and proteins may be used to block proliferation of these cancer cells in vitro or in vivo. The EDG1 polynucleotides and proteins may also be used to reduce or inhibit proliferation of colon cancer cells. The method involves increasing the levels of the EDG1 protein in the cancerous cells.

Inhibiting Proliferation with EDG1 Polynucleotides and Oligonucleotides

In one embodiment, polynucleotides encoding the EDG1 protein or a functional equivalent thereof are introduced into such cells to permit expression or overexpression of the EDG1 protein. Viral or plasmid vectors may be used to deliver the polynucleotide to the cells.

Levels of EDG1 may be increased in cancer cells by introducing a DNA fragment comprising an EDG1 polynucleotide and a promoter into the cell and expressing the EDG1 protein. Preferably, the promoter, which is operably linked to the EDG1 polynucleotide is a tissue specific promoter. The DNA fragment may be incorporated into a viral vector or into a liposome which, preferably, further comprises a molecule which targets the liposome to the cancer cell. Alternatively, levels of EDG1 are increased in the target cancer cell by delivering EDG1 into the cell via a liposome.

Viral Vector

Examples of known viral vectors are recombinant viruses which are generally based on several virus classes including poxviruses, herpesviruses, adenoviruses, parvoviruses and retroviruses. Such recombinant viruses generally comprise an exogenous gene under control of a promoter which is able to cause expression of the exogenous gene in vector-infected host cells. Recombinant viruses which can be used to transfect cells are mentioned and cited for example in a review by Mackett, Smith and Moss (1994) J Virol 49(3): 857–864.

Preferably, the virus vector is a defective adenovirus which has the exogenous gene inserted into its genome. The term "defective adenovirus" refers to an adenovirus incapable of autonomously replicating in the target cell. Generally, the genome of the defective adenovirus lacks the sequences necessary for the replication of the virus in the infected cell. Such sequences are partially or, preferably, completely, removed from the genome. To be able to infect target cells, the defective virus must contain sufficient sequences from the original genome to permit encapsulation of the viral particles during in vitro preparation of the construct.

Preferably, the adenovirus is of a serotype which is not pathogenic for man. Such serotypes include type 2 and 5 adenoviruses (Ad 2 or Ad 5). In the case of the Ad 5 adenoviruses, the sequences necessary for the replication are the E1A and E1B regions. Methods for preparing adenovirus vectors are described in U.S. Pat. No. 5,932,210, which issued in August, 1999 to Gregory et al., U.S. Pat. No. 5,985,846 which issued in November, 1999 to Kochanek et al, and U.S. Pat. No. 6,033,908 which issued in March, 2000, to Bout et al.

More preferably, the virus vector is an immunologically inert adenovirus. As used herein the term "immunologically inert" means the viral vector does not encode viral proteins that activate cellular and humoral host immune responses. Methods for preparing immunologically inert adenoviruses are described in Parks et al., Proc Natl Acad Sci USA 1996; 93(24) 13565–70; Leiber, A. et al., J. Virol. 1996; 70(12) 8944–60; Hardy s., et al, J Virol. 1997, 71(3): 1842–9; and Morsy et al, Proc. Natl. Acad. Sci. USA 1998. 95: 7866–71, all of which are specifically incorporated herein by reference. Such methods involve Cre-loxP recombination. In vitro, Cre-loxP recombination is particularly adaptable to preparation of recombinant adenovirus and offers a method for removing unwanted viral nucleotide sequences. Replication deficient recombinant adenovirus lacks the E1 coding sequences necessary for viral replication. This function is provided by 293 cells, a human embryonic kidney cell line transformed by adenovirus type. First generation adenoviruses are generated by co-transfecting 293 cells with a helper virus and a shuttle plasmid containing the foreign gene of interest. This results in the packaging of virus that replicates both the foreign gene and numerous viral proteins. More recently, 293 cells expressing Cre recombinase, and helper virus containing essential viral sequences and with a packaging signal flanked by loxP sites, have been developed (See Parks et al.) In this system, the helper virus supplies all of the necessary signals for replication and packaging in trans, but is not packaged due to excision of essential sequences flanked by loxP. When 293-Cre cells are co-transfected with this helper virus, and a shuttle plasmid (pRP1001) containing the packaging signal, nonsense "filler DNA", and the foreign gene, only an adenovirus containing filler DNA and the foreign gene is packaged (LoxAv). This results in a viral recombinant that retains the ability to infect target cells and synthesize the foreign gene, but does not produce viral proteins, for targeting cancer cells.

Methods for targeting vectors to cancer cells are described in Nakanishi T, Tamai I, Takaki A, Tsuji A. (2000) Cancer cell-targeted drug delivery utilizing oligopeptide transport activity. Int. J. Cancer. 88: 274–280, and Poul M A, Becerril B, Nielsen U B, Morisson P, Marks J D. (2000) Selection of tumor-specific internalizing human antibodies from phage libraries. *J. Mol. Biol.* 301: 1149–1161, both of which are incorporated herein in their entirety. Methods for delivering isolated oligonucleotides and polynucleotides to cells, including the nucleus of cells, are described in Lebedeva I, Benimetskaya L, Stein C A, Vilenchik M. (2000) Cellular delivery of antisense oligonucleotides. *Eur. J. Pharm. Biopharm.* 50: 101–119. Review., and Fisher K D, Ulbrich K, Subr V, Ward C M, Mautner V, Blakey D, Seymour L W. (2000) A versatile system for receptor-mediated gene delivery permits increased entry of DNA into target cells, enhanced delivery to the nucleus and elevated rates of transgene expression. *Gene. Ther.* 7: 1337–1343.

In a further embodiment an expression construct comprising the polynucleotide may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat (1991) Targeting of liposomes to hepatocytes. *Targeted Diagn. Ther* 4: 87–103). Also contemplated are lipofectamine-DNA complexes.

Inhibiting Proliferation of Cancer Cells with EDG1 Protein and Biologically Active Equivalents Thereof Proliferation of cancer cells, particularly breast cancer cells, may also be accomplished introducing an EDG1 protein or a biologically active oligonucleotide or polynucleotide derived therefrom into the cancer cell. A variety of methods exist for introducing proteins and polypeptides into cells. Such methods include, but are not limited to, "protein transduction" or "protein therapy" as described in publications by Nagahara et al. (Nagahara, et al., 1998, Nat Med. 4: 1449–52.) and in publications from the laboratory of Dowdy (Nagahara, et al., 1998, Nat Med. 4: 1449–52.; Schwarze, et al., 1999, Science, 285:1569–72.; Vocero-Akbani, et al., 2000, Methods Enzymol, 322:508–21; Ho, et al., 2001, Cancer Res, 61:474–7.; Vocero-Akbani, et al., 2001, Methods Enzymol, 332:36–49; Snyder and Dowdy, 2001, Curr Opin Mol Ther, 3:147–52.; Becker-Hapak, et al., 2001, Methods, 24:247–56.), publications which are incorporated herein by reference.

In one embodiment an eleven amino acid sequence, the "protein transduction domain" (PTD), from the human immunodeficiency virus TAT protein (Green and Loewenstein, 1988, Cell, 55:1179–88.; Frankel and Pabo, 1988, Cell, 55:1189–93.) is fused to the wild-type EDG1 protein. The purified protein is then put in contact with the surface of cells and the cells take up the wild-type EDG1 protein which functions to inhibit or suppress growth of that cell. In the case where it is desired to introduce the wild-type EDG1 protein containing the fused PTD into cells comprising a tumor in a human or animal, the protein is administered to the human by a variety of methods. Preferably, the protein is administered by injection (e.g., intravenously) or by inhalation in an aerosol.

EDG1 proteins that contain the fused PTD are preferably made by fusing the DNA sequence encoding the EDG1 protein or a functional equivalent thereof with the DNA sequence encoding the PTD. The resulting EDG1-PTD fusion gene is preferably incorporated into a vector, for example a plasmid or viral vector, that facilitates introduction of the fusion gene into a organism and expression of the gene at high levels in the organism such that large amounts of the fusion protein are made therein. One such organism in which the vector containing the fusion gene can be expressed is a bacterium, preferably *Escherichia coli*. Other organisms are also commonly used by those skilled in the art. After the fusion protein is expressed at a high level in any of these organisms, the fusion protein is purified from the organism using protein purification techniques well known to those skilled in the art.

The present invention also provides a method for inhibiting the transcriptional activity of estrogen-liganded ERα in cells, particularly in breast cancer cells. Such method comprises increasing levels of the EDG1 protein in such cells.

EXAMPLES

The invention may be better understood by reference to the following examples, which serve to illustrate but not to limit the present invention.

Methods

Tissue Culture and Transfections

Breast epithelial cells (MCF7, MCF10A, MDA-MB-231 and T47D) and PA317 amphotropic packaging cells were obtained from ATCC and maintained according to their recommended protocols. HBL100 cells were provided by Dr. David L. McCormick (I.I.T. Research Institute, Chicago, Ill.) and were maintained in Minimum Essential Medium (MEM) plus phenol red supplemented with 5% heat-inactivated fetal calf serum. CHO cells were maintained and transfected as previously described (24).

Plasmids

The EDG1 clone, pAD-GAL4-2.1-EDG1, obtained from yeast two hybrid screening contains coding sequence cloned in frame with the activation domain of GAL4 in the pAD-GAL4-2.1 phagemid vector (Stratagene, La Jolla, Calif.). The EDG1 cDNA clone was released by NcoI/XbaI digestion, blunted and inserted into SalI/SmaI-digested pCMV5 vector to make pCMV5-EDG1. The NcoI/XbaI blunted EDG1 fragment was inserted into BamHI-digested and blunted pBPSTR1 retroviral vector in the sense or antisense direction to make pBPSTR1-EDG1 or pBPSTR1-EDG1$_{AS}$ respectively. pGEX2T-EDG1, which encodes full-length EDG1 in frame with glutathione-S-transferase (GST) was constructed by inserting NcoI/XbaI blunted EDG1 fragment into BamHI digested and blunted pGEX2T (Pharmacia, Piscataway, N.J.). pEGFP-EDG1, which encodes full length EDG1 in frame with the coding sequence for Green Fluorescent Protein (GFP), was constructed by inserting NcoI/XbaI blunted EDG1 fragment into HindIII-digested and blunted pEGFP-C3 vector (Clonetech).

To make pRFP-67LR, 67LR reading frame was generated by PCR using the yeast two hybrid clone, pAD-GAL4-2.1-67LR, containing the complete coding sequence of 67LR in frame with GAL4 in the pAD-GAL4-2.1 phagemid vector, as template. Reactions were performed using Platinum Pfx DNA polymerase (GIBCO) according to the manufacturer's recommendations. The following PCR primers were used:

```
67LRf:
5' ACACAGGATCCGAATTCATGTCCGGAGCCCTTGATGTC-3',
SEQ. ID NO.: 6

67LRr:
5'-ACACAGGATCCAGTCGACTAAGACCAGTCAGTGGTTGCTCCT-3',
SEQ. ID NO.: 7.
```

The PCR fragment was purified, digested with BamHI, and cloned into BglII-digested pRFP-C1 vector.

Yeast Two Hybrid Screenings

The yeast two hybrid screenings used to identify ERα- and EDG1-interacting clones were described previously (Montano M M, Ekena K, Chang W C, Katzenellenbogen B S (1999) An estrogen receptor selective corepressor that potentiates the effectiveness of antiestrogens and represses the activity of estrogens, *Proc. Natl. Acad. Sci.* 96: 6947–6952).

In Vitro Translation and Protein-Protein Interaction Assays

In vitro transcription and translation of ERα, EDG1 or 67LR and p27/BBP were performed using the Promega TNT kit (Madison, Wis.) according to the manufacturer's recommendation. GST-pull down assays were previously described (Montano M M, Ekena K, Chang W C, Katzenellenbogen B S (1999) An estrogen receptor selective corepressor that potentiates the effectiveness of antiestrogens and represses the activity of estrogens, *Proc. Natl. Acad. Sci.* 96: 6947–6952).

Northern Blot Analysis

RNA was extracted from breast epithelial cells using Trizol (GIBCO) and was subjected to Northern Analyses as described previously (Montano M M, Jaiswal A, Katzenellenbogen B S. (1998) Transcriptional regulation of the human quinone reductase gene by antiestrogen-liganded estrogen receptor α estrogen receptor β via the electrophile/antioxidant response element. *Journal of Biological Chemistry.* 273: 25443–25449).

Retroviral-Mediated Transfection

Retroviruses were made by transfecting PA317 cells with the pBPSTR1 plasmid alone or pBPSTR1 containing EDG1 in the sense or antisense orientation. Breast epithelial cell lines were infected with retrovirus-containing supernatants in the presence or absence of 3 ug/ml tetracycline. When tetracycline was added, expression of the viral gene was inhibited. Changes in EDG1 mRNA were verified by harvesting RNA from infected cells for Northern blot analyses or by immufluorescence staining.

Immunofluoresence Staining of Breast Cells and Tissues

Breast tissue samples were fixed in formalin, embedded in paraffin, and sectioned at 5 micron thickness. To unmask epitopes we used heat-induced antigen retrieval technique using 10 mM Tris. After blocking with 10% normal goat serum, sections were incubated with EDG1 peptide 152–171) polyclonal rabbit antibody and goat, anti-rabbit IgG Alexa 488 fluorescence secondary antibody. As a negative control duplicate sections were immunostained with nonspecific rabbit IgG.

Cells grown on coverslips were fixed in paraformaldehyde. After blocking with serum, samples were incubated with EDG1 primary and seconday antibody as described above. To detect 67LR cells were immunostained using 67LR IgG monoclonal mouse antibody (Lab Vision) and goat, anti-mouse Alexa 594 secondary antibody

Anchorage Independent Growth

Four days after infection cell were detached and suspended at a concentration of $1 \times 10^4$ in medium containing 0.3% agar and then plated in a 6-well plate precoated with 0.9% agar base layer. At 24 h and 21 days after plating colonies larger than 50 µm were counted.

Example 1

Effects of EDG1 on ($E_2$)-Liganded ERα Transcriptional Activity

Estrogen Down-Regulated Gene 1 (EDG1) was identified by yeast two hybrid screenings for ER interacting proteins in breast epithelial cells. Because EDG1 interacted with Estradiol ($E_2$)-liganded ERα (FIG. 2A) we determined if EDG1 would have an effect on the transcriptional activity of $E_2$-liganded ERα. We observed down-regulation of ERα, Progesterone Receptor β (PRβ) and Retinoic Acid Receptor α (RARα) transcriptional activity in the presence of increasing amounts of expression vector for EDG1 (FIG. 2B). EDG1 did not inhibit the transcriptional activity of another transcriptional activator, VP16. Thus the effects of EDG1 on ERα transcriptional activity cannot be attributed to general breakdown of transcription. Fluorescence studies show that transfected EDG1 localizes to the nucleus (FIG. 3C).

Example 2

Detecting Cancerous Breast Epithelial Cells with Anti-EDG1 Antibody

EDG1 protein expression in breast tumor samples and adjacent normal breast tissues from 16 subjects was examined using immuncytochemical techniques. Results from representative samples are shown in FIG. 4B. As expected EDG1 expression was observed in the nuclei of endothelial blood vessels (Patient III, row 4, indicated by arrow). High levels of EDG1 protein was also detected in 15 of 16 normal breast tissue samples, specifically in the nuclei of epithelial duct cells (Patient I, II, and III, row 4). EDG1 protein was present in the epithelial cell nuclei of 1 of 3 ductal carcinoma samples in situ (Patient III, row 2) and the epithelial cell nuclei of a Bloom-Richardson Grade 1 highly differentiated mucinous infiltrating carcinoma (data not shown). In 11 out of 12 samples of poorly differentiated Grade II infiltrating ductal carcinoma (Patient I and II, row 2), there was no EDG1 protein levels in the nucleus and low levels of EDG1 protein in the cytoplasm of the cancerous cells. Thus in addition to differences in levels and spatial expression of EDG1 protein, there are differences in intracellular localization of EDG1 protein in normal breast and breast cancer tissues

Example 3

Figure 4D:
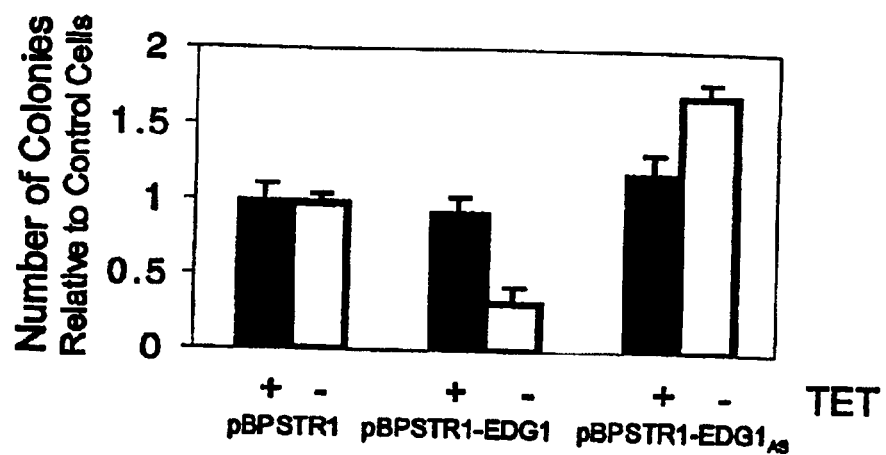

Inhibiting Anchorage-Independent Growth with a Polynucleotide Encoding EDG1 Protein Anchorage-independent growth is a necessary requirement for tumor growth and is a well-established in vitro assay for the malignantly transformed cellular phenotype. Soft agar colony formation, a measure of anchorage-independent growth, was examined in control, MCF7-EDG1 and MCF7-EDG1$_{AS}$ cells. There is a 72% decrease in colony formation as a result of increased EDG1 expression, while increased colony formation was observed in MCF7-EDG1 AS cells (FIG. 4D).

Example 4

Figure 4E:
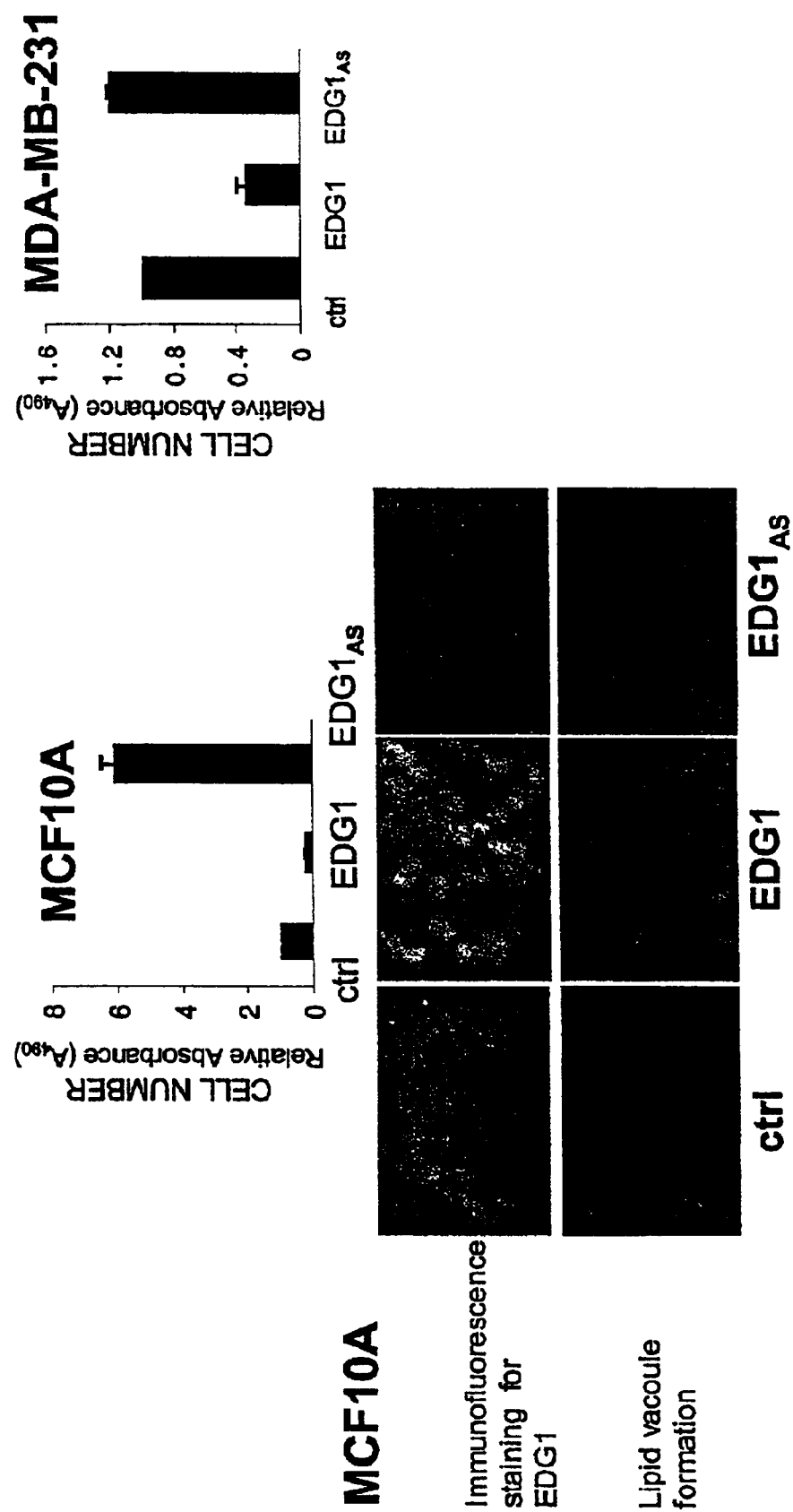

Inhibiting Proliferation of Estrogen-Receptor Negative Mammary Epithelial Cells with a Polynucleotide Encoding EDG1 Protein It was then determined if the growth inhibitory effects of EDG1 were dependent on ERα status and inhibition of ERα transcriptional activity. EDG1 and EDG1$_{AS}$ retroviruses were infected into other breast epithelial cell lines that express very low levels of ERα and ERβ protein (MCF10A), or do not express the ERα but express ERβ protein (MDA-MB-231). Decreased expression of EDG1 (0.42×) in MCF10A after infection with EDG1$_{AS}$ retroviruses is associated with 4–5-fold increase in proliferation while a slight increase in EDG1 expression (1.8×) inhibited proliferation markedly (FIG. 4E). No significant effects on proliferation of MDA-MD-231 cells, which already expresses very low endogenous levels of EDG1, was evident after infection with EDG1 $_{AS}$ retroviruses. However after infection with EDG1 retroviruses we saw a 64% decrease in proliferation (FIG. 4E). These findings suggest that some of the growth inhibitory effects of EDG1 may occur independent of ERα levels and the inhibition of ERα transcriptional activity. The importance of these findings is underscored by the fact that although the growth of some estrogen receptor (ERα) positive breast cancers can initially be hormonally manipulated, all will eventually escape hormonal control. Monica, does this mean that EDG1 can be used to treat estrogen receptor negative breast cancers as well as estrogen receptor positive breast cancer.

It was also observed an increase in lipid vacoule formation, a measure of breast epithelial cell differentiation, in MCF10A cells infected with EDG1 retroviruses (FIG. 3E).

What is claimed is:

1. An isolated polynucleotide which is 1080 nucleotides in length, wherein the nucleic acid sequence of said isolated polynucleotide is set forth in SEQ ID NO:1 or is the complete complement thereof.

2. An isolated polynucleotide which is 1080 nucleotides in length and encodes a full-length EDG1 protein, wherein the amino acid sequence of said full-length EDG1 protein is set forth in SEQ ID NO.2.

3. The isolated polynucleotide of claim 2, wherein said polynucleotide is incorporated into an expression vector, a viral genome, or a liposome, or is fused with polynucleotide which encodes a protein tag or an amino acid tag for stabilizing the EDG1 protein or for simplifying purification of the EDG1 protein, or is operably linked with a promoter which drives expression of the EDG1 protein in a cell.

* * * * *